(12) United States Patent
Richardson

(10) Patent No.: US 8,588,904 B2
(45) Date of Patent: Nov. 19, 2013

(54) PACEMAKER

(75) Inventor: Charles L. Richardson, Monroe, NC (US)

(73) Assignee: LifeScience Solutions LLC, Charlotte, NC (US)

( * ) Notice: Subject to any disclaimer, the term of this patent is extended or adjusted under 35 U.S.C. 154(b) by 1325 days.

(21) Appl. No.: 11/871,524

(22) Filed: Oct. 12, 2007

(65) Prior Publication Data

US 2008/0091244 A1 Apr. 17, 2008

Related U.S. Application Data

(60) Provisional application No. 60/851,384, filed on Oct. 13, 2006.

(51) Int. Cl.
*A61N 1/372* (2006.01)

(52) U.S. Cl.
USPC ............................................. 607/9; 607/129

(58) Field of Classification Search
USPC .................. 607/2, 4, 5, 9, 6–8, 10–18, 129
See application file for complete search history.

(56) References Cited

U.S. PATENT DOCUMENTS

| | | | | |
|---|---|---|---|---|
| 4,030,509 A | * | 6/1977 | Heilman et al. ................ | 607/17 |
| 4,998,975 A | | 3/1991 | Cohen et al. | |
| 5,111,811 A | * | 5/1992 | Smits ................................ | 607/2 |
| 5,179,946 A | * | 1/1993 | Weiss ................................ | 607/4 |
| 5,269,810 A | * | 12/1993 | Hull et al. ...................... | 607/129 |
| 5,902,324 A | | 5/1999 | Thompson et al. | |
| 6,169,918 B1 | * | 1/2001 | Haefner et al. ............... | 600/509 |
| 6,240,307 B1 | | 5/2001 | Beatty et al. | |
| 7,016,728 B2 | | 3/2006 | Thong | |
| 7,050,854 B2 | | 5/2006 | Daum et al. | |
| 2001/0031994 A1 | * | 10/2001 | Mika et al. ........................ | 607/9 |
| 2002/0082647 A1 | * | 6/2002 | Alferness et al. ................. | 607/9 |
| 2003/0010346 A1 | | 1/2003 | Paolitto et al. | |
| 2003/0083700 A1 | | 5/2003 | Hill | |
| 2003/0120318 A1 | | 6/2003 | Hauck | |
| 2004/0030356 A1 | | 2/2004 | Osypka | |
| 2004/0082974 A1 | * | 4/2004 | Holmstrom ..................... | 607/17 |
| 2004/0215253 A1 | * | 10/2004 | Weinberg .......................... | 607/9 |
| 2004/0225328 A1 | | 11/2004 | Okerlund et al. | |
| 2005/0027323 A1 | | 2/2005 | Mulligan et al. | |
| 2005/0041366 A1 | | 2/2005 | Breven et al. | |
| 2005/0043766 A1 | * | 2/2005 | Soykan et al. .................... | 607/9 |
| 2005/0065565 A1 | * | 3/2005 | Kramer et al. .................... | 607/9 |
| 2005/0096502 A1 | | 5/2005 | Khalili | |
| 2005/0182447 A1 | | 8/2005 | Schecter | |
| 2005/0216067 A1 | | 9/2005 | Min et al. | |
| 2005/0234360 A1 | | 10/2005 | Richarrdson | |
| 2005/0288727 A1 | | 12/2005 | Penner | |

(Continued)

OTHER PUBLICATIONS

Supplementary European Search Report for Application No. EP 07 85 4033 dated Dec. 20, 2010.

*Primary Examiner* — Allen Porter, Jr.

(74) *Attorney, Agent, or Firm* — Tarolli, Sundheim, Covell & Tummino LLP

(57) ABSTRACT

A system for pacing a heart includes an implantable pulse generator configured to generate electrical impulses for stimulating contraction of cardiac tissue; first, second, third, and fourth leads configured to deliver the electrical impulses to activation sites within the cardiac tissue and to detect electrical activity of the activation sites; and a controller configured to control the delivery of the electrical impulses from each of the first, second, third, and fourth leads.

33 Claims, 12 Drawing Sheets

(56) References Cited

U.S. PATENT DOCUMENTS

2006/0085039 A1* 4/2006 Hastings et al. .................. 607/9
2006/0161136 A1 7/2006 Anderson et al.
2007/0055310 A1* 3/2007 Lau .................................. 607/5
2007/0191722 A1 8/2007 Richardson et al.

* cited by examiner

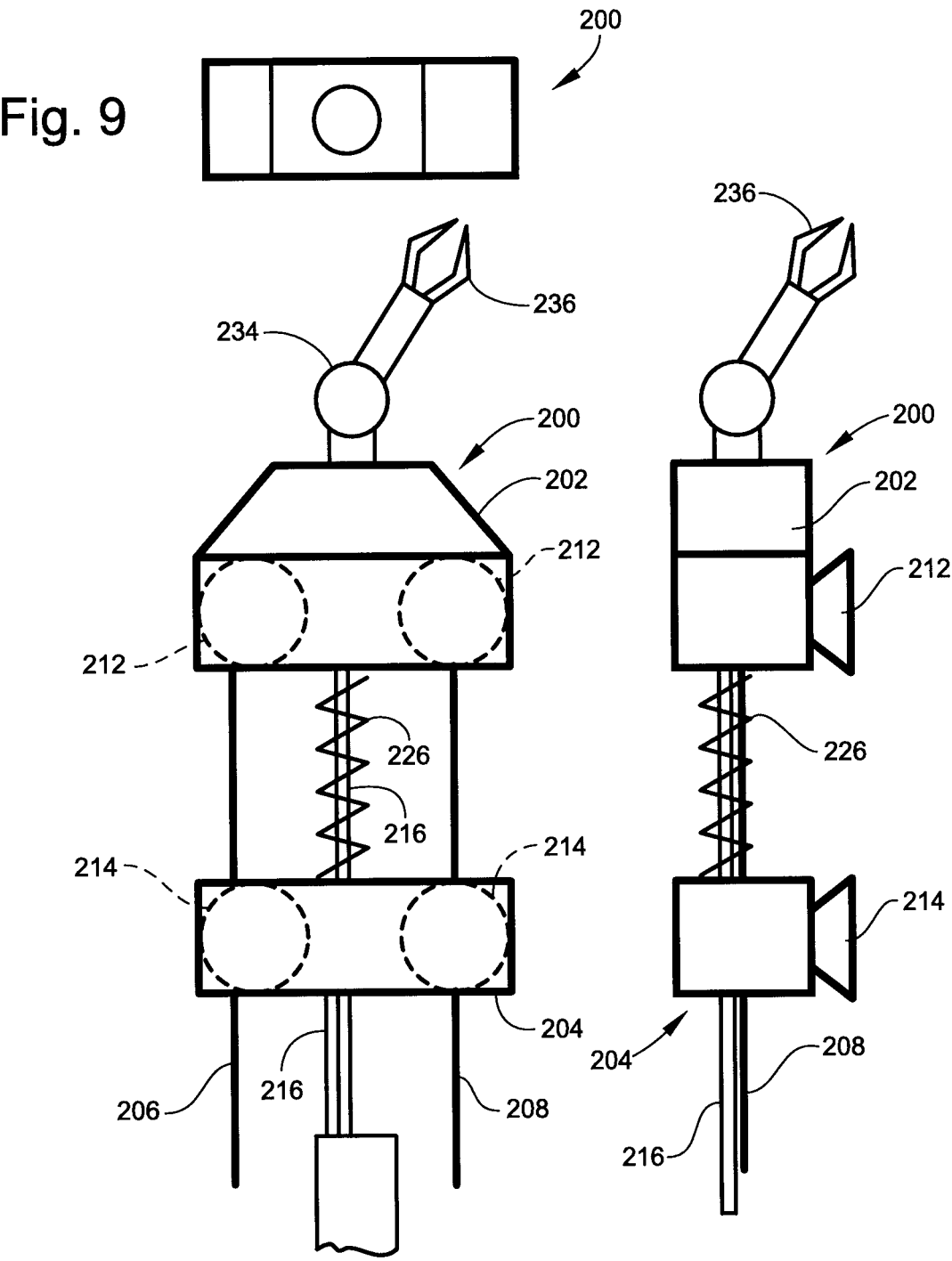

PACEMAKER

CROSS-REFERENCE TO RELATED APPLICATIONS

This application claims the benefit of Provisional Application No. 60/851,384, filed Oct. 13, 2006.

BACKGROUND

This invention relates to systems, methods and computer programs that can be used to pace and monitor the heart. More specifically, the products and processes can be used to resynchronize several areas of the heart and assess a physiological condition, such as heart failure.

A pacemaker is a medical device that regulates the beating of the heart by delivering electrical signals to one or more sites in the heart to stimulate contractions of the heart muscle. Many modern pacemakers are also capable of sensing electrical activity in the heart and are designed to stimulate the heart when no electrical activity is sensed within a certain time period. Conventional pacemakers include single chamber pacemakers and dual chamber pacemakers. Single chamber pacemakers use one lead to sense and stimulate or "pace" the right atrium or right ventricle, while dual chamber pacemakers use two leads to sense and pace both the right atrium and right ventricle. Other pacemakers include biventricular pacemakers. Biventricular pacemakers have three leads: a first lead to pace and sense the right atrium and second and third leads to pace both the right and left ventricles, respectively. Some pacemakers have four leads: first and second leads to pace and sense the left and right atriums and third and fourth leads to pace both the right and left ventricles, respectively.

According to current statistics, 1.5 million patients have been diagnosed with congestive heart failure. This disease is associated with significant morbidity and mortality. Implanted devices, including bi-ventricular pacemakers that pace both the right and left ventricles, have gained rapid acceptance as the therapeutic standard of care for preventing heart failure. Between 25 and 30% of the newly diagnosed congestive heart failure cases each year qualify for bi-ventricular pacing. This represents 75,000 patients annually. Unfortunately, of the patients who receive bi-ventricular pacing treatment, only about 60% of those patients respond. The success of ventricular resynchronization therapy relies heavily upon proper left ventricle (LV) lead placement. A large portion (about 30-40%) of the patients who are implanted receive no benefit from the device, because current methods of electrode placement require insertion through the coronary sinus, which may or may not be close to the myocardium of the left ventricle. In addition, of the patients who agree to implant, about 8% cannot receive the device because of anatomic vessel variations in the coronary sinus which do not allow placement of the leads in the vessel at all. Significant studies are underway to determine the exact location where bi-ventricular pacing leads should be placed on the heart in order to correct the 30-40% failure rate. However, since the leads of current devices are placed through the coronary sinus, a patient's anatomy may prevent optimal placement with the current system in the majority of patients.

SUMMARY OF THE INVENTION

The present invention addresses these and other challenges related to providing pacing therapy to the heart.

In one aspect, the invention features systems and methods for pacing and/or monitoring the heart. The systems and methods use an implantable pulse generator configured to generate electrical impulses that stimulate contraction of cardiac tissue using four leads. Accordingly, the first, second, third, and fourth leads can be described as leads in electrical communication with the pulse generator. The four leads are configured to deliver the electrical impulses to activation sites within the cardiac tissue and to detect electrical activity of the heart at the activation sites. The pulse generator also includes a controller configured to control the delivery of the electrical impulses from each of the first, second, third, and fourth leads. Although the leads may be placed on any of the four heart chambers, generally, one lead is placed in the right atrium, a second lead is placed in the right ventricle, a third lead is placed on the surface of the left ventricle, and a fourth lead is also placed on the surface of the left ventricle posterior to the third lead (e.g., the third lead can be placed on an anterior surface of the left ventricle and the fourth lead can be placed on a posterior surface of the left ventricle). The atrium or atria are stimulated first (either by the patient's natural heartbeat or by the pulse generator), and a fraction of a second later, the left and right ventricles are stimulated. The ventricles can be stimulated at the same time or at various times that, preferably, allow the ventricles to contract in better synchrony. When the contractions are not synchronized, the symptoms of heart failure can be worse; when the contractions of the ventricles are timed correctly, the heart pumps more efficiently. Lead placement "on" or "in" the heart or a chamber of the heart refers to epicardial placement of a distal segment of the lead. Similarly, activation sites "within" the cardiac tissue refers to sites within the myocardium that can be stimulated by electrodes at the distal ends of the placed leads.

The pulse generator may be programmed with pacing parameters that direct the sensing and pacing functions of the pulse generator. Examples of pacing parameters include one or more of: pacing mode; amplitude, polarity, timing and pulse width of the electrical impulses; ventricular sensitivity; atrial sensitivity; and a rate of pacing the heart. The pacing parameters may be modified or reprogrammed as needed. A monitoring system may be provided to receive diagnostic data associated with the heart from the implantable pulse generator and to modify one or more programmable pacing parameters based on the diagnostic data. Diagnostic data, for example, may include impedance measurements, telemetry and holter measurements, and measurements indicative of heart failure. From the diagnostic data, a medical condition, such as heart failure, may be determined. For example, one can assess volumes within the heart (e.g., ventricular volume) from impedance measurements acquired by the four leads epicardially or endocardially across different vectors of the heart. From an analysis of the volumes, a condition such as heart failure can be diagnosed and assessed. Accurate volume measurements are potentially invaluable in monitoring the progression of disease and the impact of therapy.

A communication relay device that is wirelessly coupled to the implantable pulse generator may be provided to: (1) relay the diagnostic data from the implantable pulse generator to the monitoring system and (2) relay commands for modifying the pacing parameter from the monitoring system to the implantable pulse generator. The controller delivers the electrical impulses to the atrium and ventricles of the heart according to a programmed pacing mode. The programmed pacing mode may be selected from a variety of rate-responsive and non-rate responsive pacing modes, including those described using a standard NBG code developed by the North American Society of Pacing and Electrophysiology (NASPE) and the British Pacing and Electrophysiology Group (BPEG). Other pacing mode standards can also be used. Examples of NBG pacing modes that can be executed by the controller include, but are not limited to: DOD, OOI, DVI, OOO, VDD, VVI, VOO, AAI, and AOO pacing modes. The controller may be configured to direct the first, second, third, and fourth leads to continuously deliver electrical impulses to the activation sites, regardless of the speed and/or beating rhythm of the heart. The controller may be configured to direct at least two of the first, second, third, and fourth leads to stimulate the left and right ventricles of the heart at the same time or at varied times. Preferably, the left and right ventricles will contract in synchrony.

In one aspect, the invention features methods for pacing the heart by providing an implantable pulse generator having first, second, third, and fourth leads; identifying viable areas of the heart from an image of the heart; and connecting the first, second, third and fourth leads to activation sites in the myocardium located within the viable areas. As in other embodiments, the implantable pulse generator can be configured to generate electrical impulses for stimulating contraction of cardiac tissue. Identifying viable areas can include a step of identifying areas of the heart that are, or that are among, the most contractile (e.g., electrically contractile). The image can be captured non-invasively (e.g., by computed tomography (CT), magnetic resonance imaging (MRI), positron emission tomography (PET), and echocardiography (Tissue Doppler). The methods can further include the steps of delivering the electrical impulses through the first, second, third, and fourth leads to activation sites within the cardiac tissue and sensing electrical activity of the heart using each of the leads. The leads can be placed in any of the configurations described herein.

In another aspect, the invention features methods and systems to improve and/or optimize lead placement and to provide adequate therapy for patients who either cannot receive bi-ventricular pacing (e.g., patients anatomically unsuited for implantation) or patients who have failed conventional bi-ventricular therapy with leads positioned through the coronary sinus. Optimized placement of the four leads of the implantable pulse generator can be achieved by identifying viable areas of the heart from an image of the heart and connecting the leads to activation sites located wholly or partially within the viable areas. For example, the leads may be connected to the heart by placing the first lead on the surface of the right atrium, placing the second lead on the surface of the right ventricle, placing the third lead at a posterior site in the left ventricle, and placing the fourth lead at an anterolateral site in the left ventricle. The viable areas are electrically contractile areas of the heart and may be the most, or among the most, electrically contractile areas. Viable areas can be identified from an image captured using a non-invasive imaging technique such as CT, MRI, PET, and echocardiography (e.g., Tissue Doppler). Either a computer program or skilled practitioner can select activation sites for placement of the leads within the viable areas or areas that include at least some electrically contractile tissue. Because the activation sites are located at least partially within viable areas, ventricular contraction can be synchronized (or resynchronized) using the first, second, third, and fourth leads to pace the heart at the activation sites and with various timing.

In a further aspect, the invention features methods and systems that enable robotic placement of the four leads at activation sites that have been determined to be suitable (e.g., most optimal) for resynchronization of the heart. Using a robotic mechanism to place the leads enables precise positioning of the leads at the activation sites. Current biventricular pacing technology does not ensure precise positioning of leads and it is believed that this limitation can lead to heart failure in patients who have received biventricular pacemakers. The robot mechanism includes a mechanical arm and a controller in communication with the mechanical arm. The controller is configured to control the movement of the mechanical arm. Motion sensors coupled to the controller detect movements of a human hand (e.g., a surgeon's hand to which they are attached), encode the movements as an electrical signal, and transmit the electrical signal to the controller. Based on the electrical signal, the controller controls the movements of the mechanical arm to replicate the movements of the human hand. Mechanical appendages mounted to an end of the mechanical arm include surgical tools for operating on the patient. Once placement locations have been determined by non-invasive methods, the robotic mechanism can be used to implant a pulse generator in the patient through a mini-thoracotomy or through an incision in a diaphragm. Thus, the implantation can avoid the coronary sinus and is less invasive than implantations that require thoracotomy or median sternotomy. The first, second, third, and fourth leads are positioned underneath the skin of the patient's abdomen and tunneled to an epicardial surface of the heart. The leads are then connected to the heart (e.g., to one or more activation sites) using the robotic mechanism. For example, the robotic mechanism may attach a first lead to an activation site located on the right atrium, a second lead to an activation site located on the right ventricle, a third lead to a posterior activation site on the left ventricle, and a fourth lead attaches to an anterolateral activation site on the left ventricle. As robotic placement of the pulse generator does not require conventional thoracotomy or median sternotomy, recovery should be rapid and most patients should be discharged from the hospital within about two to three days.

DESCRIPTION OF DRAWINGS

The invention may be best understood by reference to the following description taken in conjunction with the accompanying drawing figures in which:

FIG. 7 is a top view of the rover of FIG. 6;

FIG. 8 is a side view of the rover of FIG. 6;

FIG. 9 is a front view of the rover of FIG. 6;

DETAILED DESCRIPTION

Figure 1:
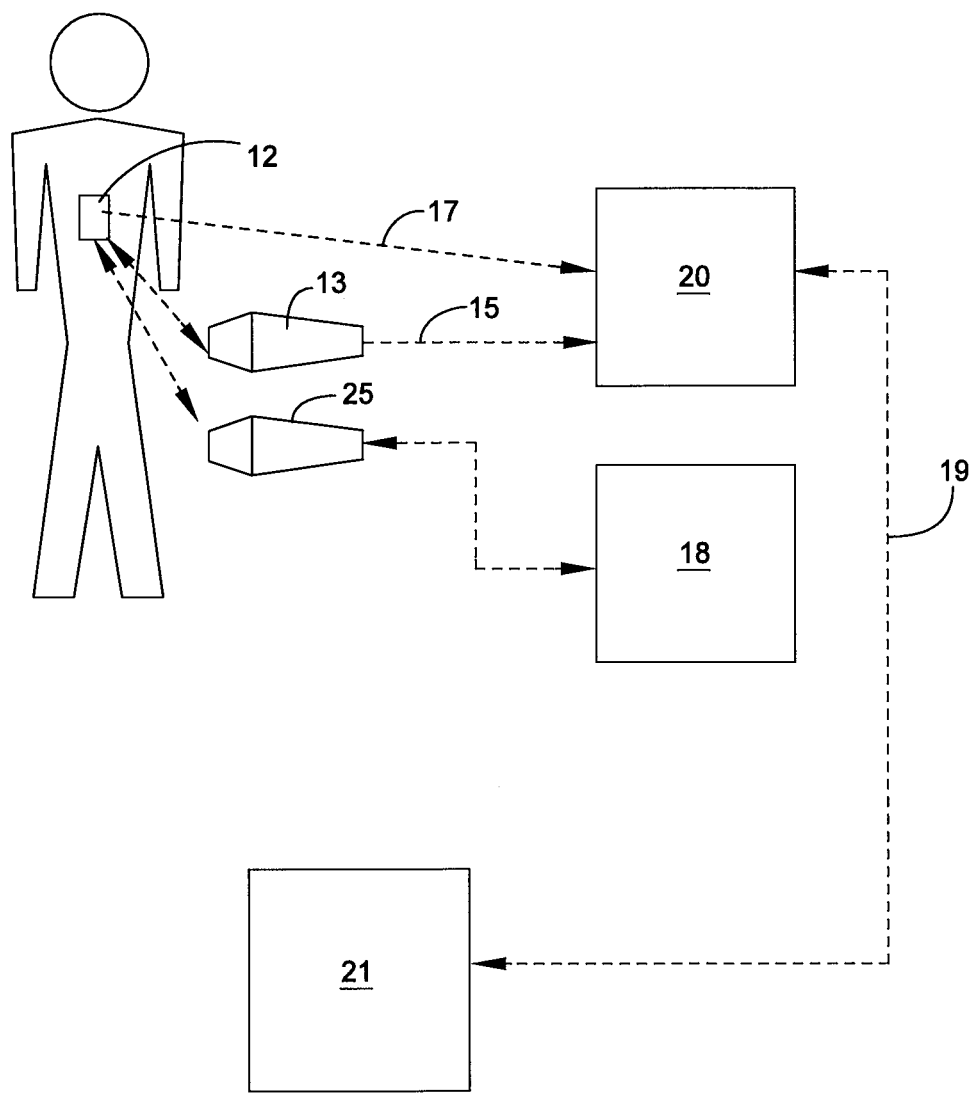
FIG. 1 is a block diagram of a system for pacing and monitoring a heart.

Referring to the drawings wherein identical reference numerals denote the same elements throughout the various views, FIG. 1 depicts a heart monitoring and pacing system 10 including an implantable pacemaker 12 for pacing and monitoring a patient's heart, a physician interface unit 18 in communication with the pacemaker 12, and a monitoring system 20 for monitoring patient data acquired by the pacemaker 12.

The monitoring system 20 is used to receive, store, and optionally process data from the pacemaker 12. The monitoring system 20 can include a computer, microprocessor, or central processing unit operating under software control, with associated data storage means such as flash memory, RAM, EEPROM, hard disk, floppy disks, CD or DVD-ROM, etc., and a transceiver or other data communication means (e.g. a TCP/IP network adapter or modem). In use, the monitoring is placed in communication with the pacemaker 12, for example using a relay unit 22 such as the illustrated handheld wand. The relay unit 22 includes an antenna, power source, data storage means, and transceiver compatible with the with that of the pacemaker 12 (such as an induction coil). In use, the relay unit 22 receives data from the pacemaker 12, for example by inductive coupling at short range. The data is then either stored for later transfer to the monitoring system 20, or immediately transferred to the monitoring system 20. The transfer occurs through a communications link 15 such as a cable, infrared transmitter, or wireless link (e.g. BLUETOOTH wireless protocol). Optionally, communication between the pacemaker 12 and the monitoring system 20 may be through a radio frequency (RF) communications link 17 of a known type.

Optionally, the monitoring system 20 may be configured to receive data from the pacemaker 12 and then transfer that data over a remote communications path 19 such as a wireless or wired packet-switched network (e.g. a local area network, a wide area network, or Internet), over telephone lines using a modem, or through satellite connection. The remote communications link may be encrypted for security purposes. The data may be received by a data server 21 or monitoring service at a remote location. Optionally, the data may be received from the pacemaker 12 and then stored by the monitoring system 20 for later transmission to the data server 21.

A physician interface unit 18 may be provided (also referred to as a programmer or programming system). This comprises a computer 23 (e.g. a laptop microcomputer, a desktop computer, a tablet PC, or a personal data assistant) and a relay unit 25 similar to the relay unit 22 described above, or other suitable communications link compatible with the pacemaker 12. At the computer 23, a skilled practitioner develops software that controls the pacing and monitoring functions of the pacemaker 12. The software may be tailored according to the specific medical needs or conditions of the patient who has received (or is about to receive) the pacemaker 12. The physician interface unit 18 transmits software programs to the pacemaker 12 through the relay unit 25. The software programs include instructions that control the pacing and monitoring functions of the pacemaker 12. The physician interface unit 18 may also communicate with the pacemaker 12 to read statistics logged by the pacemaker 12, display marker signals received from the pacemaker, maintain a log of activities, print reports, record standard programs for future use, reprogram the pacemaker 12 with safe values in emergency situations, and the like.

Figure 2A:
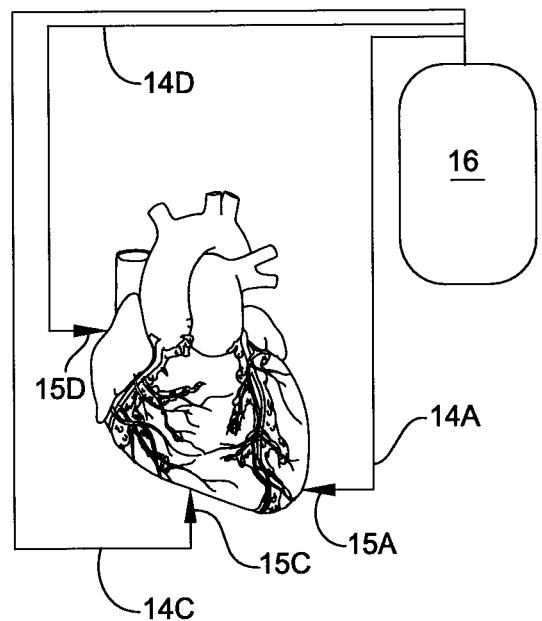
FIG. 2A is a schematic view of a pulse generator of the system of FIG. 1, showing the leads thereof implanted to the anterior aspect of a heart.
Figure 2B:
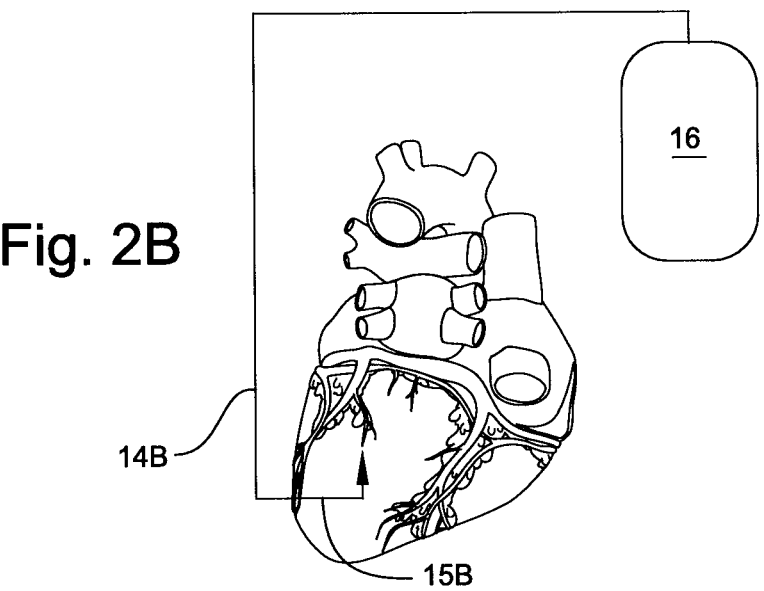
FIG. 2B is a schematic view of a pulse generator of the system of FIG. 1, showing the leads thereof implanted to the posterior aspect of a heart.

Referring to FIGS. 2A and 2B, the pacemaker 12 includes a programmable pulse generator 16 and four leads 14A-d, respectively (collectively referred to as leads 14). It is noted that FIG. 2A shows three of the leads and FIG. 2B shows the fourth lead. The proximal ends of the leads 14 are in electrical communication with the pulse generator 16, and the distal ends of the leads 14 are configured to be in physical contact with activation sites within the heart. The distal ends of the leads 14 include electrodes 15A-d, respectively (collectively referred to as electrodes 15). The electrodes 15 may be either unipolar or bipolar and function to produce electrical signals and detect electrical activity. In some variations, each of the electrodes 15 may include two electrodes: a sending electrode for sending an electrical signal to an activation site and a sensing electrode for sensing electrical activity from the activation site.

As shown in FIGS. 2A and 2B, the first and second leads 14A and 14B are placed on the left ventricle at anterior and posterior sites, the third lead 14C is placed on the right ventricle near the intraventricular septum, and the fourth lead 14D is placed on the right atrium. In other variations, the third lead 14C is placed elsewhere (e.g., on the left or right ventricle). In general, different combination of leads 14 may be placed on any of the chambers at various locations to improve, and preferably optimize, contraction of the heart and cardiac output. The success of ventricular resynchronization therapy relies heavily upon proper left ventricle lead placement. Using two or more leads to pace the left ventricle should improve cardiac function compared to conventional techniques that pace the left ventricle using only one lead because it enables more sites in the left ventricle to be synchronized and allows volumetric monitoring and heart failure monitoring More particularly, posterior LV lead placement should be more effective for hemodynamic augmentation than either lateral or anterior positioned leads.

The pulse generator 16 stores a software program received from the physician interface unit 18. Directed by the software program, the pulse generator 16 produces control signals and delivers the control signals to the leads 14. In response to receiving the control signals, the leads 14 deliver electrical impulses to the activation sites for stimulating contraction of the heart. The leads 14 can also sense electrical activity at the activation sites and generate sensing signals that encode the electrical and timing characteristics of the sensed electrical activity. The pulse generator 16 processes the sensor signals to control pacing and to generate a picture of the electrical activity of the heart as detected from within the heart (an electrogram or "EGM"). An EGM is different from an electrocardiogram ("ECG"), which is a picture of the heart's electrical activity detected from the surface of the skin. The pacemaker 12 may optionally include additional leads that are dedicated to sensing electrical activity of the heart from which EGM data is generated.

The relay unit 22 receives the recorded EGM data from the pacemaker 12 over a wireless channel and transmits the data to the monitoring system 20. The monitoring system 20 includes one or more computers for analyzing the EGM data and/or other data received from the pacemaker 12 via the relay unit 22. Based on the physical and biological properties measured from the data or from a direct analysis of the data itself, a skilled practitioner can determine if the heart is operating normally or as desired. An analysis of the data can also reveal signs of damage to the heart; reveal problems with the electrical conduction system; assist in diagnosing a disease (e.g., heart failure (e.g., congestive heart failure>>; and monitor the effects of the pacemaker 12. For example, an analysis of the data may prompt a skilled practitioner to reprogram one or more pacing functions of the pacemaker 12.

Figure 3:
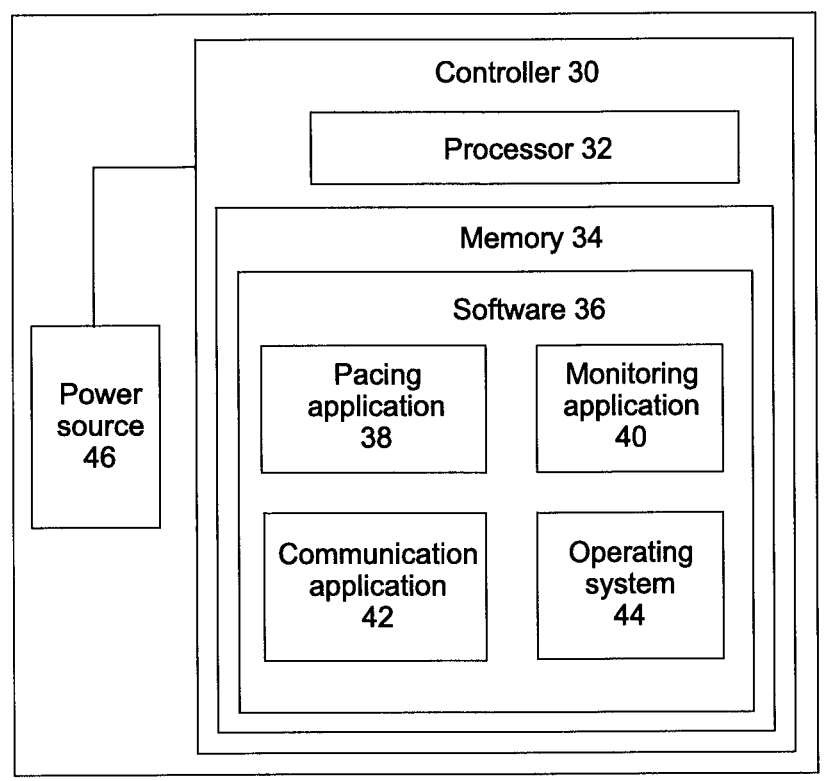
FIG. 3 is a block diagram of a pulse generator for use with the system of FIG. 1.

In some embodiments, the monitoring system 20 and the physician interface unit 18 are integrated to form one system that can communicate with the pacemaker 12 either directly or via the relay unit 22. Referring to FIG. 3, a block diagram shows the pulse generator 16 of the pacemaker 12 in further detail. The pulse generator 16 includes a controller 30 and a power source 46 (e.g., a battery) for providing power to the controller 30. The controller 30 includes one or more processor(s) 32 (which we may refer to simply as "processor 32") and memory 34 for storing software 36. The processor 32 executes software 36, which includes a pacing application 38, a monitoring application 40, a communication application 42, and an operating system 44 (e.g., such as, UNIX or WINDOWS XP). The pacing application 38 controls the pacing and sensing functions of the pacemaker. The monitoring application controls the acquisition of EGM information performed by the leads 14 and the transmission of recorded ECG information to the relay unit 22. The communication application 42 includes one or more routines used in implementing a communication protocol (e.g., a TCP/IP protocol) which allows the controller 30 to communicate over wireless channels with the physician interface unit 18 and the relay unit 22.

The pacing application 38 includes programmable parameters that control different aspects of pacing, including the pacing mode (i. e., a set of instructions that determine the timing and order of sensing and pacing of various chambers of the heart and the conditions under which one or more of the chambers are sensed and/or paced), properties of pacing signals delivered by each of the leads 14 (e.g., amplitude and pulse width), and a pacing rate. Table 1 lists exemplary programmable parameters and values that may be specified in the pacing application 38. The values of the parameters shown in Table 1 below are for the sake of illustration. They may be varied to suit a particular application.

TABLE 1

| Pacemaker Parameters | |
| --- | --- |
| Pacing Mode | DOD, VDD, DDI, DVI, DOO VVI, VOO, AAI, AOO, OFF |
| Basic Rate | From 30 to 170 min$^{-1}$ (+1–1 min$^{-1}$) in steps of 2 min$^{-1}$ |
| Upper Tracking Rate | From 60 to 180 min$^{-1}$ (+1–1 min$^{-1}$) in steps of 2 min$^{-1}$ |
| Upper Tracking Rate Mode | Fixed-Ratio AV Block, Electronic Wenckebach |
| Anti-PMT algorithm | On/Off |
| Atrial Pulse Width | From 0.06 ms to 0.15 ms (+/−0.015 ms) in steps of 0.03 ms |
| | From 0.20 ms to 1.00 ms (+/−0.03 ms) in steps of 0.05 ms |
| | From 1.10 ms to 1.50 ms (+/−0.03 ms) in steps of 0.10 ms |
| Atrial Pulse Amplitude | From 0.5 V to 10.0 V (+/−10%) in steps of 0.5 V |
| Pacing Polarity | Unipolar/Bipolar |
| Atrial Sensitivity | From 0.1 mV to 5.0 mV (+/−20%) in steps of 2.0 mV |
| Atrial Sensing Polarity | Unipolar/Bipolar |
| Atrial Refractory Period | From 100 ms to 500 ms (+/−5 ms) in steps of 10 ms |
| Post Ventricular Atrial Refractory Period | From 100 ms to 600 ms (+/−5 ms) in steps of 10 ms |
| Atrial Refractory Extension | Off, from 50 to 200 ms (+/−5 ms) in steps of 50 ms |
| Ventricular Pulse Width | From 0.06 ms to 0.15 ms (+/−0.015 ms) in steps of 0.03 ms |
| | From 0.20 ms to 1.00 ms (+/−0.03 ms) in steps of 0.05 ms |
| | From 1.10 ms to 1.50 ms (+/−0.03 ms) in steps of 0.10 ms |
| Ventricular Pulse Amplitude | From 0.5 V to 10.0 V (+/−10%) in steps of 0.5 V |
| Ventricular Pacing Polarity | Unipolar/Bipolar |
| Ventricular Sensitivity | From 0.2 mV to 10.0 mV (+/−20%) in steps of 0.8 mV |
| Ventricular Sensing Polarity | Unipolar/Bipolar |
| Ventricular Refractory Period | From 100 ms to 600 ms (+/−5 ms) in steps of 10 ms |
| Ventricular Blanking Period | From 10 ms to 50 ms (+/−2 ms) in steps of 10 ms |
| Hysteresis Rate | Off, from 4 to 60 min$^{-1}$ (+/−1 min$^{-1}$) in steps of 4 min$^{-1}$ |
| Hysteresis Search | On/Off |
| Post Pacing AV Delay | From 10 to 350 ms (+/−5 ms) in steps of 10 ms |
| Post Sensing AV Delay | From 10 to 350 ms (+/−5 ms) in steps of 10 ms |
| AV Adaptive Enable | On/Off |
| Minimum AV Delay | From 10 ms to 180 ms (+/−5 ms) in steps of 10 ms |
| Mode Switching Atrial rate | from 120 min$^{-1}$ to 250 min$^{-1}$ in steps of 10 min$^{-1}$ |
| EMG Recording/ Histograms | Automatic detection algorithms |
| Rate Response | Sensor to determine activity level |

The following provides a description of the pacing parameters listed in Table 1. The Pacing Mode parameter specifies the method of pacing performed by the pacemaker 12. The method of pacing is described using a five-position standard NBG code developed by the North American Society of Pacing and Electrophysiology (NASPE) and British Pacing and Electrophysiology Group (BPEG). The NBG code, which is summarized in Table 2, specifies the chamber(s) paced, the chamber(s) sensed, a sensing response, programmability, and anti-tachyarrhythmia functions.

TABLE 2

NASPE/BPEG Generic Pacemaker Code (NBG)

| Position I | Position II | Position III | Position IV | Position V |
|---|---|---|---|---|
| Pacing Chamber(s) | Sensing Chamber(s) | Response(s) to Sensing | Programmability | Anti-Tachycardia Function(s) |
| O = None | O = None | O = None | O = None | O = None |
| A = Atrium | A = Atrium | I = Inhibited | P = Programmable | P = Pacing |
| V = Ventricle | V = Ventricle | T = Triggered | M = Multiprogrammable | S = Shock |
| D = Dual (A + V) | D = Dual (A + V) | D = Dual (I + T) | C = Communicating | D = Dual (P + S) |
|  |  |  | R = Rate Modulation |  |

Often, the fifth position (i.e., Position V) is dropped from codes corresponding to pacing methods in which no anti-tachycardia functions are used, resulting in a four-position code. For example, the code DDDRO may be expressed as DDDR. Similarly, both the fourth and fifth positions (Positions IV and V) are often dropped from codes corresponding to pacing methods in which no programmability and anti-tachycardia functions are used, resulting in a three-position code. For example, the code DDDOO can be expressed as DDD.

If the Pacing Mode parameter is set to DDD, the pacemaker 12 senses and paces in both the atrium and ventricles to achieve double synchronization. If the Pacing Mode parameter is set to DVI, the pacemaker 12 senses in the ventricles (but not in the atrium), paces in both the atrium and ventricles, and inhibits pacing in the ventricles if it senses electrical activity in the ventricles. If the Pacing Mode parameter is set to DDI, the pacemaker 12 senses and paces in both the atrium and ventricles and inhibits pacing if it senses electrical activity in the ventricles. If the Pacing Mode parameter is set to VDO, the pacemaker 12 senses in both the atrium and ventricles and paces in the ventricles to achieve double synchronization. If the Pacing Mode parameter is set to DOO, the pacemaker 12 paces in the atrium and ventricles but does not sense in any chamber. If the Pacing Mode parameter is set to VVI, the pacemaker 12 senses and paces in the ventricles and inhibits pacing when it senses electrical activity in the ventricles. If the Pacing Mode parameter is set to VOO, the pacemaker 12 paces in the ventricles but does not sense in any chamber. If the Pacing Mode parameter is set to AAI, the pacemaker 12 senses and paces in the atrium only and inhibits pacing when it senses electrical activity in the atrium. If the Pacing Mode parameter is set to AOO, the pacemaker 12 paces in the atrium only and does not sense in any of the chambers. If the Pacing Mode parameter is set to Off, the pacemaker 12 does not pace or sense in any of the chambers.

In addition to the pacing modes listed in Table I, the Pacing Mode parameter can be programmed to other modes described using the NBG code shown in Table 2. For example, the Pacing Mode parameter may be set to a rate-responsive pacing mode, examples of which include, but are not limited to: DDDR, DDIR, DVIR, DOOR, VDDR, VVIR, VOOR, AAIR, and AOOR. The Pacing Mode parameter can also be programmed to modes described using other codes, including standard and non-standard codes.

The pulse generator 16 directs the leads 14 to deliver electrical impulses to one or more chambers of the heart according to the programmed pacing mode specified by the Pacing Mode parameter. Although many conventional pacing modes are designed for pacemakers having three or fewer leads, different placement combinations of the four leads 14 in the chambers enables the pacemaker 12 to operate in conventional pacing modes. In some variations, the pacemaker 12 operates in the DDD pacing mode using a lead placement configuration in which the first lead 14A is placed on the right atrium, the second lead 14B is placed on the right ventricle, and the third and fourth leads 14C-D, are each placed on the left ventricle. In other variations, the pacemaker 12 operates in the DOD pacing mode using a lead placement configuration in which the first lead 14A is placed on the right atrium, the second lead 14B is placed on the left ventricle, and the third and fourth leads 14C-D, are each placed on the right ventricle. In further lead-placement configurations, depending on the pacing mode used and physiological conditions of the heart, two or more of the leads may be placed on anyone of the right atrium, the left atrium, the right ventricle, and the left ventricle.

The Basic Rate parameter indicates the lowest sustained regular rate at which the pacemaker 12 paces the heart. Typically, the pacemaker 12 begins pacing when the patient's intrinsic rate falls below this value. For example, in Table 1, the basic pacing rate of the pulse generator 16 is programmable between 30 bpm and 170 bpm in increments of at most 2 bpm in both single-chamber and dual-chamber modes. In some embodiments, the resulting rate is within ±1% of the programmed basic pacing rate.

The Upper Tracking Rate parameter specifies the upper rate at which the pacemaker 12 tracks atrial activity when programmed in DDD or VDD modes. Should a patient develop an atrial tachyarrhythmia, such as atrial fibrillation or flutter, the generator acts to limit ventricular pacing. In the event the patient develops an atrial rhythm higher than the upper tracking rate, the pulse generator 16 responds with an appropriate A-V block mechanism, specified by the upper tracking rate mode parameter. As shown in Table 1, the upper tracking rate is programmable in the range of 60 to 180 bpm in increments of 2 bpm. In some implementations, the actual upper tracking threshold rate is within ±1% of the programmed upper tracking rate.

The Upper Tracking Rate Mode parameter specifies how the pulse generator 16 responds to atrial rates detected above the programmed Upper Tracking Rate parameter. For example, as shown in Table 1, the pulse generator 16 may respond with either a Fixed-Ratio A-V Block or with "Electronic Wenckebach". When the Fixed-Ratio A-V Block option is selected and atrial sensed rates are above the programmed Upper Tracking Rate parameter, the pulse generator 16 applies a protected 2:1 fixed-ratio A-V block when the calculated ventricular-ventricular interval is shorter than the period corresponding to the programmed Upper Tracking Rate parameter. Otherwise, the block is extended until the instantaneous ventricular interval is greater than the period corresponding to the programmed Upper Tracking Rate parameter. Extending the block when the instantaneous ventricular-ventricular interval is shorter than that corresponding Upper Tracking Rate parameter increases safety by protecting the ventricle from the fastest atrial tachycardia.

When the "Electronic Wenckebach" Block option is selected and atrial sensed rates are above the programmed Upper Tracking Rate parameter, the pulse generator 16 applies a standard "Electronic Wenckebach" algorithm for ventricular protection. In operation, "Electronic Wenckebach" algorithm is applied when the calculated ventricular-ventricular interval is greater than the period corresponding to the programmed Upper Tracking Rate parameter. In such situations, the interval A-V is increased to match the V-V interval to the corresponding value of the programmed Upper Tracking Rate parameter. Compared to a fixed-ratio A-V block, an "Electronic Wenckebach" block simulates a more physiological response of the heart for protecting the ventricles from inappropriately high atrial rates.

The Anti-PMT Algorithm (Pacemaker Mediated Tachycardia Termination Algorithm) parameter specifies whether or not the pacemaker incorporates an algorithm to detect the potential presence of pacemaker-mediated tachycardia (PMT). The algorithm is programmable as On or Off. In some embodiments, a situation of potential PMT occurs when the delay between a ventricular paced event and an atrial sensed event is shorter than 400 ms. When the Pacing Mode parameter is programmed with either a VDO or DDD mode and the pulse generator 16 detects symptoms of PMT during ten consecutive cycles, the post ventricular atrial refractory period (PVARP) is increased to 400 ms for one cycle. If unsuccessful, the attempt is repeated every 127 cycles until the symptoms of PMT are eliminated.

PMT may be observed in patients paced in dual-chamber modes because of slow retrograde AV conduction mechanisms. When the sensing of an atrial signal by the pacemaker initiates ventricular tracking behavior that results in retrograde activation of the atrium, another ventricular output is triggered, and V-A conduction is perpetuated. The PMT-termination algorithm may be required if the programmed PVARP is not sufficient to prevent the sensing of retrograde P-waves.

The Atrial Pacing Pulse Width parameter specifies the width of the electronic impulses that are delivered to the atrium. For example, according to Table 1, the pulse width for atrial pacing pulses issued by the pulse generator 16 is programmable according to the following ranges: a first range between 60 µs and 150 µS in steps of 30 µs, a second range between 150 µs and 1000 µs in steps of 50 µs, and a third range between 1000 µs and 1500 µs in steps of 100 µs. In some embodiments, the actual atrial pulse width is within ±15 µs of the programmed value for pulse widths less than or equal to 150 µs and within ±30 µs of the programmed value for pulse widths greater than 150 µs.

The Atrial Pulse Amplitude parameter specifies the amplitude of the electronic impulses that are delivered to the atrium. For example, according to Table 1, the atrial pulse amplitude is programmable within the range of 0.5 V to 10.0 V in steps of 0.5 V, at most. In some implementations, the actual atrial pulse amplitude is within ±10% of the programmed value and 0.2 V.

The Atrial Pacing Polarity parameter specifies whether the electrical impulses delivered from the pacemaker 12 to the atrium are unipolar or bipolar. When the Atrial Pacing Polarity parameter is programmed to be unipolar, pulses having a negative polarity are delivered to the atrium. When the Atrial Pacing Polarity parameter is programmed to be bipolar, pulses having positive and negative polarities are delivered to the Atrium. The Atrial Pacing Polarity parameter may be programmed independently from the Ventricular Pacing Polarity parameter, which is described below. Enabling the selection between unipolar or bipolar pacing polarities provides higher flexibility in programming the pulse generator 16 to achieve appropriate performance. Independent selection of pacing polarity on each chamber provides flexibility in the selection of pacing leads and pacing characteristics.

The Atrial Sensitivity parameter specifies the amplitude of electricity in the atrium that the pulse generator 16 must detect to make a determination that a contraction in the atrium has occurred. The Atrial Sensitivity parameter can be programmed within a suitable range of standard atrial sensitivities to allow appropriate operational settings of the pulse generator 16 and to enable assessment of the performance of the implanted leads 14. For example, according to Table 1, the Atrial Sensitivity parameter is programmable from 0.1 mV to 5.0 mV in steps of 2 mV, at most. In some implementations, the actual atrial sensitivity of the pacemaker 12 is within ±20% of the programmed Atrial Sensitivity parameter.

The Atrial Sensing Polarity parameter specifies whether the sensing polarity of the pulse generator 16, when sensing electrical impulses of the atrium, is unipolar or bipolar. When the Atrial Sensing Polarity parameter is programmed to be unipolar, the pacemaker 12 senses the atrial signal between a negative-voltage terminal and ground. When the Atrial Sensing Polarity parameter is programmed to be bipolar, the pacemaker 12 senses the atrial signal between a negative-voltage terminal and a positive-voltage terminal. The Atrial Sensing Polarity parameter can be programmed independently from 5 the Ventricular Sensing Polarity parameter, which is described below. The ability to select between unipolar and bipolar sensing polarities provides higher flexibility in programming the pacemaker 12, which can, in turn, enhance performance.

The Atrial Refractory Period parameter specifies periods of times in which atrial sensing is disabled on single-chamber atrial-only modes after atrial paced or sensed events. An atrial refractory period during atrial-only modes may be used to prevent inappropriate multiple detections of the same atrial event. In some embodiments, the atrial refractory period is programmable in the range of 100 ms to 500 ms in 10 ms steps with a tolerance of ±5 ms.

The Post Ventricular Atrial Refractory Period (PVARP) parameter specifies periods of times in which atrial sensing is disabled in dual modes after paced or sensed ventricular events. The PVARP may used to increase or maximize the probability that a retrograde atrial depolarization will fall within the atrial refractory period to reduce the possibility of initiating a pacemaker-mediated tachycardia. In some embodiments, the PVARP parameter is programmable in the range of 100 ms to 600 ms in 10 ms steps with a tolerance of ±5 ms.

The Atrial Refractory Extension parameter specifies a time over which the post ventricular atrial refractory period is extended after the detection of premature ventricular contractions (PVCs). The pacemaker 12 determines the occurrence of a PVC when it detects a ventricular event (sensed or stimulated) without detecting a previous atrial event. The Atrial Refractory Extension parameter is either programmed Off or programmed to increment the PVARP by an extension period specified in the pacing application 38. For example, the Atrial Refractory Extension parameter may increment the PVARP by an extension period within a range of 50 ms to 200 ms in steps of 10 ms. When the Atrial Refractory Extension parameter is programmed Off, the PVARP is not incremented. In some embodiments, when Atrial Refractory Extension parameter is applied, the actual atrial refractory extension period is within ±5 ms of the programmed value. Application of the Atrial Refractory Extension parameter may be used to prevent the initiation of a tachycardia provoked by the pacemaker (PMT). A ventricular event (sensed or stimulated) not preceded by an atrial event (sensed or stimulated) can generate a retrograde conduction. If the pacemaker senses this P retrograde signal and initiates an AV period that, in the end, stimulates the ventricle, another P retrograde signal can be generated that initiates an AV, and so on. This cycle can initiate tachycardia, and the pacemaker can participate in that through the monitoring of the retrograde P signal. As noted, this phenomenon is called PMT. In this case, the extension of the PVARP, if it is of an adequate value, avoids the inhibition of an atrial pulse owing to the sensing of a retrograde P. In DDI mode, application of the Atrial Refractory Extension parameter may help to avoid the inhibition of an atrial stimulus due to the sensing of a retrograde P.

The Ventricular Pacing Pulse Width parameter specifies the width of the electronic impulses delivered from the pacemaker 12 to the ventricles. For example, according to Table 1, the pulse width for atrial pacing pulses issued by the pulse generator 16 is programmable according to the following ranges: a first range between 60 μS and 150 μs in steps of 30 μS, a second range between 150 μs and 1000 μs in steps of 50 μS, and a third range between 1000 μs and 1500 μs in steps of 100 μs. In some embodiments, the actual ventricular pulse width is within ±15 μS of the programmed value for pulse widths less than or equal to 150 μS and within ±30 μs of the programmed value for pulse widths greater than 150 μs.

The Ventricular Pulse Amplitude parameter specifies the amplitude of the electronic impulses that are delivered to the ventricles. For example, according to Table 1, the Ventricular Pulse Amplitude parameter is programmable within the range of 0.5 V to 10 V in steps of at least 0.5 V. In some embodiments, the actual ventricular pulse amplitude is ±10% of the programmed value or about 0.2 V.

The Ventricular Pacing Polarity parameter specifies whether the electrical impulses delivered from the pacemaker 12 to the ventricles are unipolar or bipolar. When the Ventricular Pacing Polarity parameter is programmed to be unipolar, pulses having a negative polarity are delivered to the ventricles. When the Ventricular Pacing Polarity parameter is programmed to be bipolar, pulses having positive and negative polarities are delivered to the ventricles the Ventricular Pacing Polarity parameter may be programmed independently from the Atrial Pacing Polarity parameter. The ability to select between unipolar and bipolar sensing polarities provides better flexibility in programming the pacemaker 12, which can, in turn, enhance performance. Furthermore, independent selection of pacing polarity on each chamber provides flexibility in the selection of pacing leads and pacing characteristics.

The Ventricular Sensitivity parameter specifies the amplitude, timing, and pulse width of electricity in the ventricles that the pacemaker 12 must detect to make a determination that the ventricles have contracted. The Ventricle Sensitivity parameter can be programmed within a suitable range of standard ventricular sensitivities to allow appropriate operational settings of the pulse generator 16 and to enable assessment of the performance of the implanted leads 14. For example, according to Table I, the Ventricle Sensitivity parameter is programmable from 0.2 mV to of 10.0 mV in steps of 0.8 mV, at 15 most. In some embodiments, the actual ventricular sensitivity of the pacemaker 12 is within ±20% of the programmed Ventricle Sensitivity parameter.

The Ventricular Sensing Polarity parameter specifies whether the sensing polarity of the pulse generator 16, when sensing electrical impulses in the ventricles, is unipolar or bipolar. When the Ventricle Sensing Polarity parameter is programmed to be unipolar, the pacemaker 12 senses the ventricular signal between a negative-voltage terminal and ground. When the Ventricle Sensing Polarity parameter is programmed to be bipolar, the pacemaker 12 senses the ventricular signal between a negative-voltage terminal and a positive-voltage terminal. The Ventricular Sensing Polarity parameter can be programmed independently from the Atrial Sensing Polarity parameter, which is described above. The ability to select between unipolar and bipolar ventricle sensing polarities provides better flexibility in programming the pacemaker 12, which can, in turn, enhance performance.

The Ventricular Refractory Period parameter specifies periods of time in which ventricular sensing after ventricular events, whether paced or sensed, is blocked. In modes DDD, DDI, and VDD, the ventricular refractory period is less than or equal to the post ventricular atrial refractory period (PVARP), which is described above. In some embodiments, the ventricular refractory period is programmable in the range of 100 ms to 600 ms in 10 ms steps, with a tolerance of ±5 ms.

The Ventricular Blanking Period parameter specifies periods over which the pacemaker disables ventricular sensing on dual modes after pacing the atrium. For example, the Ventricular Blanking Period parameter may be programmed in the range of 10 ms to 50 ms in steps of 10 ms. In some implementations, the actual ventricular blanking period of the pacemaker 12 is within ±2 ms of the programmed value.

The Hysteresis Rate parameter specifies the rate at which the pacing rate is decreased if the pacemaker 12 senses that the patient's intrinsic rate is above the programmed Basic Rate parameter. This parameter may be either programmed Off or programmed to a value (e.g., a value in the range from 4 to 60 bpm in steps of 4 bpm). If the Hysteresis Rate parameter is programmed Off, no change to the pacing rate is applied in response to a sensed event.

In AAI and DDD modes, the pacemaker 12 changes the rate of pacing according to the Hysteresis Rate parameter in response to an atrial sensed event. In VVI and VDD modes, the pacemaker 12 changes the rate of pacing according to the Hysteresis Rate parameter in response to a ventricular sensed event. In DOD mode, a PVC may cause the pacemaker 12 to change the rate of pacing according of the Hysteresis Rate parameter.

Table 3 illustrates the way in which the Hysteresis Rate parameter is applied for various pacing modes. In Table 3, BR represents the Basic Rate parameter, H represents the Hysteresis Rate parameter and AVp represents the calculated AV Delay parameter, which is described in further detail below in connection with Equation 1.

TABLE 3

Application of Hysteresis Rate

| Mode | Event that determines the use of hysteresis | Period with hysteresis | Calculation form |
|---|---|---|---|
| DDD | As | TA_A | $\dfrac{6000}{(BR + H)}$ |
|  | VinA1 | TV_A | $\dfrac{6000}{(BR + H)} - AVp$ |

TABLE 3-continued

Application of Hysteresis Rate

| Mode | Event that determines the use of hysteresis | Period with hysteresis | Calculation form |
|---|---|---|---|
| VDD | Vs | TV_V | $\dfrac{6000}{(BR+H)}$ |
| VVI | Vs | TV_V | $\dfrac{6000}{(BR+H)}$ |
| AAI | As | TA_A | $\dfrac{6000}{(BR+H)}$ |

In some embodiments, the actual hysteresis rate is within ±1 bpm of the programmed value.

The Hysteresis Search parameter specifies whether or not the pacemaker 12 detects hysteresis. If the Hysteresis Rate Change parameter is programmed Off, the Hysteresis Search parameter is automatically toggled Off. If, however, the Hysteresis Rate parameter is not programmed to be Off, the Hysteresis Search parameter may be toggled either On or Off. When the Hysteresis Search parameter is toggled On, after a predefined number of cycles (e.g., 700 cycles) have been completed without sensing intrinsic activity in the corresponding chamber, the pacemaker 12 decreases pacing at the hysteresis rate specified by the Hysteresis Rate parameter for a predetermined number of consecutive cycles (e.g., five cycles).

The Post Pacing AV Delay parameter specifies a delay between the time at which the pacemaker 12 paces the atrium and the time at which the pacemaker 12 performs the next pacing function. For example, in DDD, DDI, DVI and DOO modes, the pacemaker 12 paces the ventricles only after the atrium is paced and the paced AV delay expires, unless inhibited by a sensed ventricular event. As shown in Table I, for example, the Post Pacing AV Delay in response to atrial paced events is programmable between 10 ms and 350 ms in steps of 10 ms. In some implementations, the actual Post Pacing AV delay 20 is within ±5 ms of the programmed value.

The Post Sensing AV Delay parameter specifies a delay between the time at which the pacemaker 12 senses an atrial event (e.g., contraction) and the time at which the pacemaker responds to the sensed atrial event. For example, in DDD and VDD modes, the pacemaker 12 paces the ventricles only after an atrial event is sensed and the Post Sensing AV Delay expires, unless inhibited by a sensed ventricular event. As shown in Table I, for example, the Post Sensing AV Delay in response to atrial sensed events is programmable between 10 ms and 350 ms in steps of 10 ms. In some implementations, the actual Post Sensing AV Delay is within ±5 ms of the programmed value.

A difference between the Post Pacing AV Delay parameter and the Post Sensing AV Delay parameter is generally set to a predefined value (e.g., ranging between 0 to 70 ms) such that the Post Sensing AV Delay parameter is smaller than the Post Pacing AV Delay parameter. When the auricle is stimulated, atrial depolarization occurs after the atrial pacing pulse, and when the atrium (e.g., an atrial auricle) is sensed, the depolarization begins before it is sensed. Therefore, to have a hemodynamic situation in which (1) both the atrium and ventricles are paced and in which (2) the atrium is sensed and the ventricles are paced, the Post Sensing AV Delay parameter is programmed to be smaller than Post Pacing AV Delay parameter.

The AV Delay Adaptation parameter specifies a rule for determining the atrioventricular delay (i.e., the time that the pacemaker 12 waits after detecting (or initiating) an atrial event before pacing the ventricle). The AV Delay Adaptation parameter can be toggled On and Off.

When the AV Delay Adaptation parameter is programmed On and an atrial event is sensed, the AV resultant period can be calculated as:

$$AV_A = \text{Max}\left(AV_m, AV_S * \frac{T_{AA}}{T_B}\right) \quad (1)$$

where $AV_m$ is the programmed minimum AV, $AV_s$ is the programmed post sensing AV, $T_{AA}$ is the measured atrial interval, and $T_B$ is the period corresponding to the basic rate. In some implementations, the actual adapted AV is within ±5 ms of the value calculated according to Equation 1. To mimic the normal physiologic adaptation of the P-R interval, the pacemaker 12 may be programmable to adapt the AV delay to changes in the preceding atrial interval.

The Minimum AV Delay parameter specifies the minimum AV delay to be introduced when the AV Delay Adaptation parameter is programmed On. For example, in Table 1, the Minimum AV Delay parameter is programmable in a range between 10 ms and 180 ms, in steps of 10 ms. In some implementations, the actual Minimum AV Delay is within ±5 ms of the programmed value.

The Mode Switching parameter specifies an atrial rate indicative of atrial arrhythmia. In response to detecting an atrial rate at or above the Mode Switching parameter, the pacemaker 12 changes pacing operations to reduce patient symptoms associated with atrial arrhythmia. For example, as shown in Table 1, the Mode Switching parameter may specify an atrial rate ranging between 120 and 250 bpm in steps of 10 bpm.

The EGM Recording/Histograms parameter specifies the algorithm(s) by which the pacemaker 12 acquires and stores electrocardiographic data for diagnostic purposes while pacing (or monitoring) the heart according to the programmed parameters. The algorithms may include automatic detection algorithms.

The Rate Response parameter specifies the type of activity sensor used to determine different levels of physical activity. The pulse generator 16 adjusts pacing according to the level of activity determined by the sensor. In some implementations, the activity sensor is bonded to the inside of the pacemaker's outer case and detects pressure waves caused by muscle movement or body motion. The pacemaker's circuitry translates these pressure waves into electrical signals, which are processed by the pulse generator 16 to adjust the pacing rate up or down.

The monitoring application 40 includes software routines for measuring the impedance of the atrium and the ventricles. When the monitoring application 40 executes an impedance measuring operation, one of the leads 14 (e.g., lead 14A) sends an electrical impulse to the heart, and one or more different leads (e.g., leads 14B-d) detect the electrical impulse. As the leads that detect the electrical impulse, they measure the electrical impedance over the distances between the activation sites to which they are attached and the activation site to which the sending lead (e.g., lead 14A) is attached. From the measurements of impedance over different vectors of the heart, the pulse generator 16 reconstructs the volumes of the various chambers of the heart and the heart itself. Through an analysis of the volumes, a condition of the heart, such as heart failure, may be diagnosed. The leads 14 may acquire impedance measurements at sites that are located on the epicardial surface, located endocardially (i.e., inside the heart), or from a combination of both epicardial and endocardial sites. For example, the leads of a conventional pacemaker can be modified to acquire impedance measurements across different vectors of the heart in the manner described above. The leads 14 may also acquire telemetry and holter measurements. The monitoring application 40 includes a threshold measurement routine for determining the pacing and sensing thresholds in atrial and ventricular channels using the four leads 14. The routine includes functions that determine the pacing and sensing thresholds automatically and functions that enable a person to manually determine the pacing and sensing thresholds. The pacing threshold is the minimum amount of energy (or battery power) required to stimulate contractions of the heart. Determining the pacing threshold is important to ensure consistent pacing and to maximize the pacemaker's battery life. The sensing threshold is the minimum amplitude of electrical activity of the heart that the pacemaker must detect to make a determination that a contraction has commenced. Determining the sensing threshold is important to make sure that the pacemaker only paces the heart when needed.

The monitoring application 40 stores, among other data, the atrial and ventricular impedances and pacing and sensing thresholds, in memory 34. When the controller 30 receives a request from the relay unit 22 to transmit the data acquired by the monitoring application 40, the controller retrieves the data from the memory 34 and executes the communication application 42 to transmit the data from the pacemaker 12 to 15 the relay unit 22. In some embodiments, the duration of the data transmission operation is on the order of minutes if no communication errors occur. When executing the data transmission operation, the relay unit 22 is able to detect transmission errors in real time and set a visual or sound alarm that allows the patient or practitioner to relocate or reposition the relay unit 22 in a manner that enables more reliable transmission (e.g., by moving the relay unit 22 closer to the patient). In this case, the communication application 38 restarts transmission operation from the last cluster of bytes successfully transferred to the relay unit 22.

Figure 4:
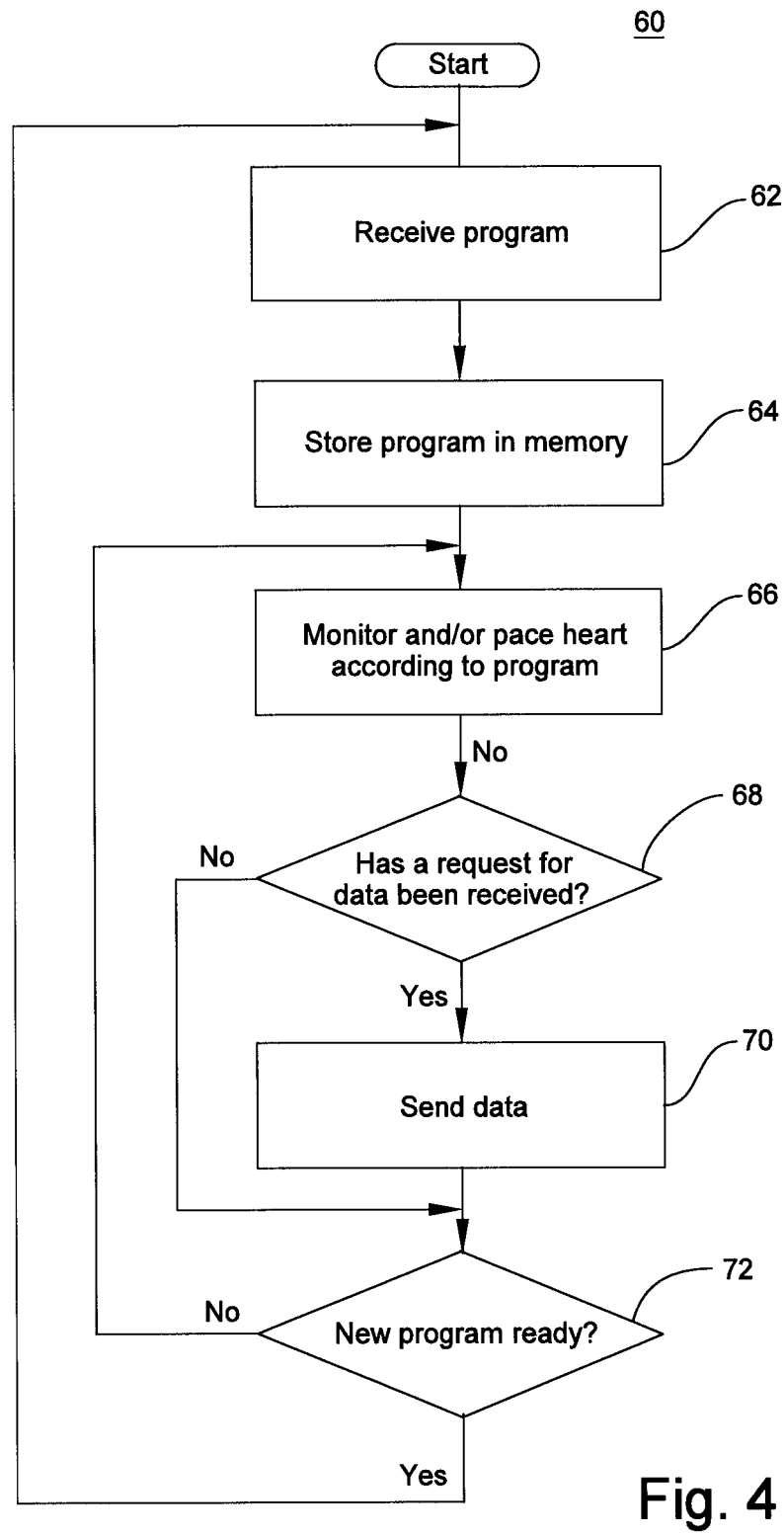
FIG. 4 is a flowchart of a pacemaker process.

Referring to FIG. 4, a process 60 performed by the controller 30 of the pacemaker 20 is shown. The controller receives (block 62) a program from the physician interface unit 18 and stores (block 64) the program in memory. The program includes programmable parameters, such as those shown in Tables 1 and 2, applicable to the pacing application 38, the monitoring application 40, or both. The program may also include instructions to turn off the monitoring functions and perform only pacing functions or vice versa. As directed by the program, the controller 30 directs (block 66) the monitoring and pacing of the heart and listens (block 68) for a request from either the relay unit 22 or the physician interface unit 18. If a request for data is received, the controller 30 sends the requested data to the device (either to the relay unit 22 or the physician interface unit 18) that sent the request. The controller 30 continues to direct the monitoring and pacing functions specified by the program until it determines (block 72) that the physician interface unit 18 has a new program ready to be downloaded. The controller 30 receives the new program (block 62) and the process 60 is repeated.

Figure 5:
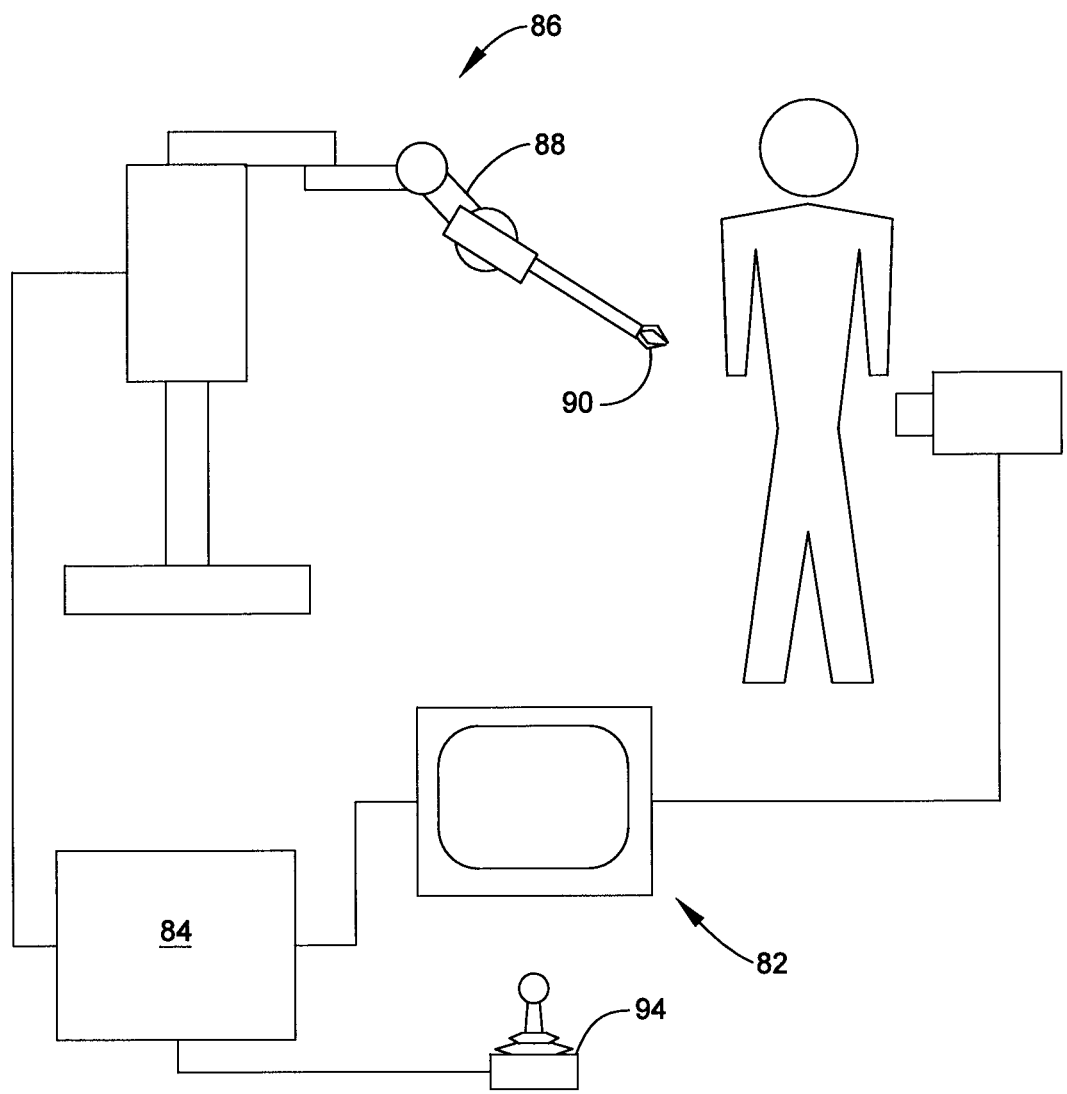
FIG. 5 is a block diagram of a system for implanting a pacemaker into a subject.
Figure 6:
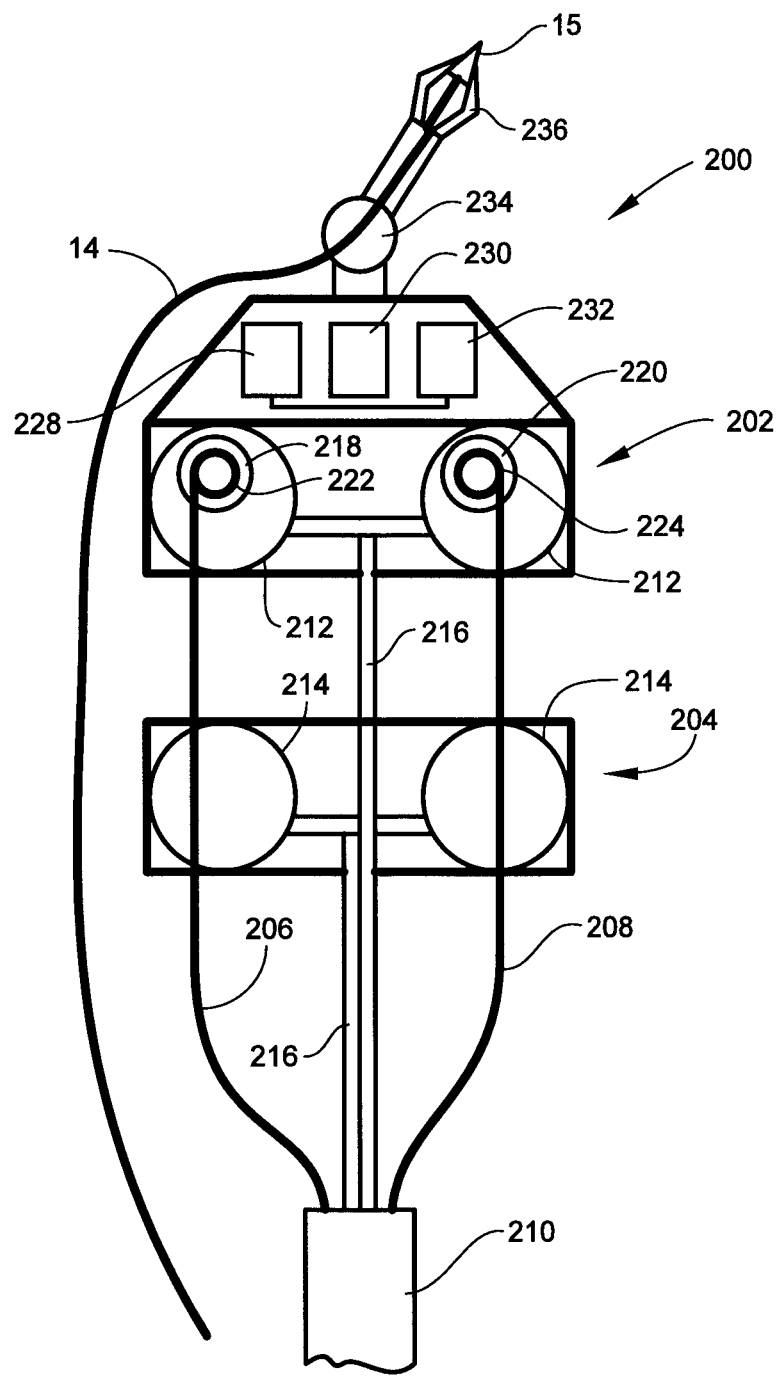
FIG. 6 is a schematic cross-sectional view of a rover constructed in accordance with an aspect of the present invention.

Referring to FIG. 5, a system for implanting the pacemaker 12 into a patient includes an imaging system 82, a robotic mechanism 86, motion sensors 94 (e.g. wrist instruments or a joystick as illustrated), and a control computer 84 in data communication with the motion sensors 94, the imaging system 82, and the robotic mechanism 86. The robotic mechanism 86 includes tools 90 attached to an robotic arm 88 having multiple degrees of freedom of movement, powered by suitable actuators (not shown). Examples of tools 90 include, but are not limited to, scalpels, saws, scissors, a needle and suture, clamps, forceps, electrode implantation devices, and other surgical tools. Robotic mechanisms of this type are sold under the name DAVINCI by Intuitive Surgical, Inc. Sunnyvale, Calif. 94086 USA. The imaging system 82 generates images of the patient's heart. Examples of the imaging system 82 include, but are not limited to, Doppler echocardiogram imaging systems, computed tomography (CT) imaging systems, magnetic resonance imaging (MRI) systems, fluoroscopy imaging systems, ultrasound imaging systems, and positron emission tomography (PET) imaging systems.

FIGS. 6-9 illustrate an exemplary remote control rover 200 that may be used separately from, or in conjunction with, the robotic mechanism 86 described above. The rover 200 comprises a front section 202 and a rear section 204 which are interconnected in at least two locations laterally spaced-apart from a central longitudinal axis "A". In the illustrated example, left and right cables 206 and 208 run from the front section 202 through the rear section 204, and then continue rearwards where they are contained inside a sheath 210. Collectively the sheath 210 and its contents form a tether which may be used to withdraw the rover 200 from a patient. The front and rear sections 202 and 204 are the functional components, and may be enclosed or otherwise incorporated into a common frame or housing (not shown) if desired. Each section 202 and 204 includes at least one suction cup (denoted front and rear suction cups 212 and 214, respectively) mounted on its bottom surface. The suction cups 212 and 214 are connected to flexible vacuum hoses 216 which run in the sheath 210 and are connected to a suitable controllable vacuum source such as a vacuum pump (not shown).

Means are provided for controlling and manipulating the distance between the front and rear sections 202 and 204, as well as their relative orientation. In the illustrated example, left and right motors 218 and 220 with drums 222 and 224 are provided so that the left and right cables 206 and 208 can be controllably reeled and unreeled, drawing the rear section 204 closer to the front section 202, or pushing the rear section 204 away from the front section 202 (the cables 206 and 208 have sufficient stiffness to transmit compressive forces). Optionally, a spring 226 (not shown in FIG. 6; shown in FIGS. 7-8) may be provided which is compressed as the cables 206 and 208 are reeled in. The cables 206 and 208 may then be released by allowing the drums 222 and 224 to "free-wheel", thus permitting the spring to force the front and rear sections 202 and 204 apart.

The front section 202 of the rover 200 contains a battery 228, a controller 230, and a wireless transceiver 232 for communication with an external control station (such as control computer 84). A miniature manipulator arm 234 is carried at the end of the rover 200 and operated by the controller 230. It holds a tool 236, such as a scalpel, saw, scissor, needle and suture, clamp, forceps, electrode implantation device, or other surgical tool. As shown, the manipulator arm 234 is equipped with a gripper which can be used to hold and implant a lead 14 with the attached electrode 15.

Figure 10A:
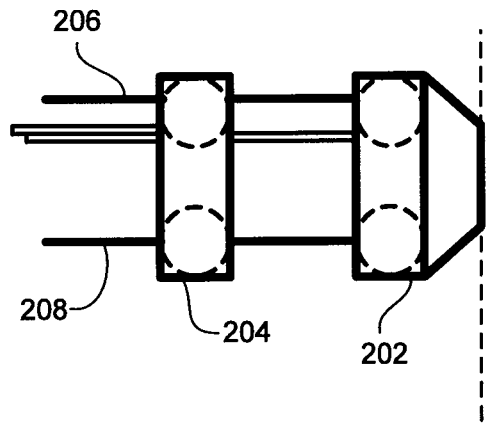
FIGS. 10A-10C are sequential views depicting the straight-line motion of the rover of FIG. 6.
Figure 10B:
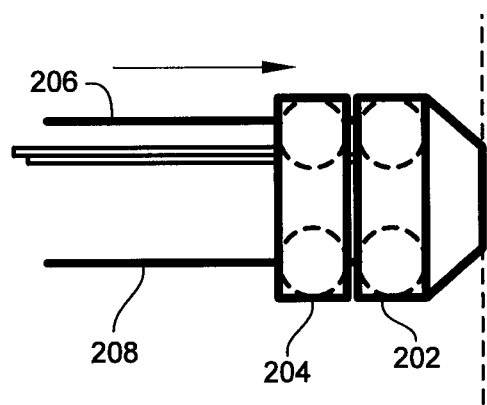
Figure 10C:
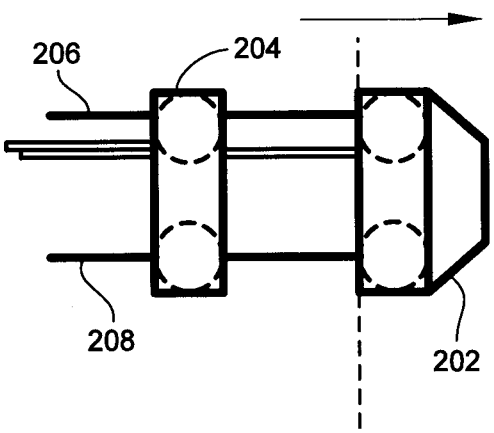

The operation of the rover 200 will now be explained with reference to FIGS. 10A through 10C. In FIG. 10A, the front and rear suction cups 212 and 214 are both applied, securing the rover 200 in a starting position the heart or other organ (not shown), with the front and rear sections 202 and 204 spaced apart from each other. To move forward, the rear suction cups 214 are released, and the rear section 204 is drawn towards the front section 202 until it is resting against the front section 202, as shown in FIG. 10B. This may be done by reeling the cables 206 and 208 into the front section 202. Next, the rear suction cups 214 are applied and the front suction cups 212 are released. The front section 202 is then extended away from the rear section. This may be done by unreeling the cables 206 and 208 (if cables of suitable stiffness are selected, the compression forces may be transmitted through them). Optionally, the spring 226 may be released, propelling the front section 202 away from the rear section 204. These steps may be repeated to move the rover 200 forwards in a series of "steps" or "hops".

Figure 11A:
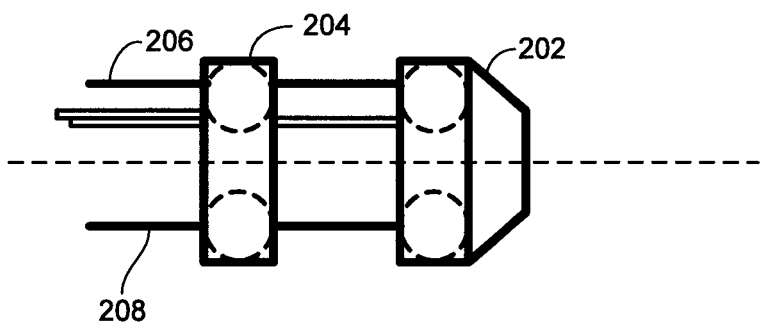
FIGS. 11A-11C are sequential views depicting the turning motion of the rover of FIG. 6.
Figure 11B:
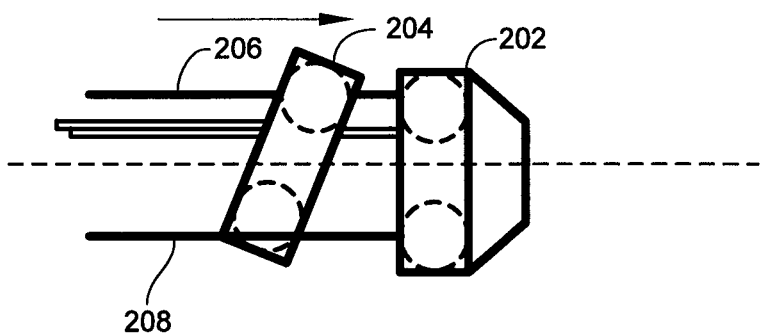
Figure 11C:
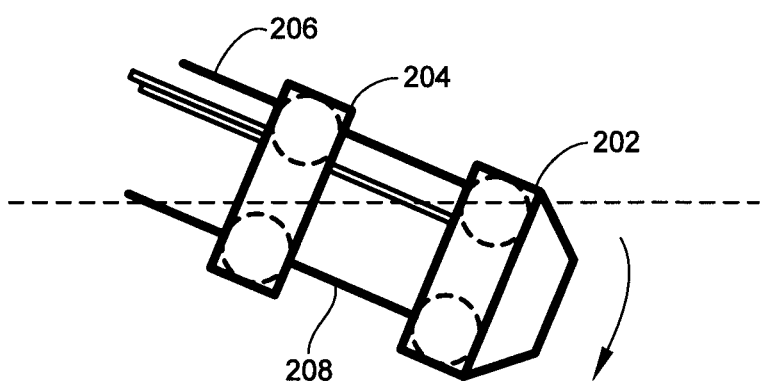

The orientation of the rover 200 can be altered using a similar procedure, as shown in FIGS. 11A-11C. In FIG. 11A, the front and rear suction cups 212 and 214 are both applied, securing the rover 200 in a starting position the heart or other organ (not shown), with the front and rear sections 202 and 204 spaced apart from each other, and the axis A of the rover 200 aligned in a first direction. To turn, the rear suction cups 214 are released, and the rear section 204 is drawn asymmetrically towards the front section 202 so that one side of it is closer to the front section than the other, as shown in FIG. 11B. This may be done by differentially reeling the cables 206 and 208 into the front section 202. Next, the rear suction cups 214 are applied and the front suction cups 212 are released. The front section 202 is then extended away from the rear section 204. This may be done by unreeling the cables (if cables of suitable stiffness are selected, the compression forces may be transmitted through them). Optionally, the spring 226 may be released, propelling the front section 202 away from the rear section. In either case, the cables 206 and 208 are allowed to extend until the front section 202 and the rear section 204 are in the same relative position as shown in FIG. 1A (i.e. parallel to each other). However, since the rear section 204 has been previously rotated, this return to the "nominal" position causes the front section to skew to the side, as shown in FIG. 11C. This procedure may be carried out to turn the rover 200 in either direction. Once a turn has been completed, the rover 200 may be advanced using the "straight-line" procedure described above.

These steps for generating motion can be carried out in any sequence and can be modified to suit a particular application. For example, the rear section 204 may be provided with suitable actuators to move along the cables 206 and 208, rather than having them reeled in and out by the front section. Furthermore, the front and rear sections 202 and 204 could be moveable relative to each other in more than one axis. Finally, any type of actuator or interconnecting member could be substituted for the cables 206 and 208.

The rover 200 offers several potential advantages when compared with percutaneous approaches. Namely: (1) Access to the entire heart gives the surgeon the ability to place the LV leads freely; (2) LV leads may be robotically placed in the most hemodynamically advantageous positions based on both preoperative and intraoperative studies; (3) LV leads may be robotically placed in the most electrophysiologically positions based on both preoperative and intraoperative studies; (4) Reproducibility of the procedure allows it to be done with an immediate success rate in a very expeditious manner; (5) Inherent stabilization—adhesion to the heart surface means that rover 200 is not disturbed by the beating motion of the heart or other organs; (6) Localized sensing: one or more sensors can be carried by the rover 200 to measure physical properties directly from the heart surface, and map the readings to the exact location; (7) Absence of lung deflation—the flexibility of the insertion point allows a subxiphoid approach that does not breach the lung space (creating the potential for outpatient procedures); (8) Enhanced Access—locomotion allows the rover 200 to reach any location on the heart surface or other organ tissues and easily change operative fields from a single incision; and (9) low cost—the small, potentially disposable rover 200 may cost far less than robotic teleoperative surgical systems currently used.

The robotic mechanism 86 and/or the rover 20 operate as follows. From the images, various sites of the heart are selected as activation sites for receiving the leads 14 of the pacemaker 12. The motion sensors 94 detect movements of a surgeon's hand and encode the 20 movements as electrical motion signals. The motion sensors 94 transmit the motion signals to the controller 84. If the robotic arm 88 is used alone, the control computer 84 controls the movement of the robotic arm 88 using a control signal that activates the actuators. The control computer 84 generates the control signal based on the motion signal it receives from the motion sensors 94 to cause the robotic mechanism 86 to replicate the movements of the surgeon's hand. Under control of the control computer 84, the robotic mechanism 86 implants the pacemaker 12 inside the patient and, using an epicardial approach, connects the leads 14 to the activation sites on and within the patient's heart. If the rover 200 is used, the robotic arm 88 may be used as described above to make an incision, and place the rover 200 on the epicardial surface of the heart. The same motion sensors 94 may then be used to send commands to the rover 200 to administer therapy (e.g. lead placement) under control of the physician. Alternatively, the surgeon may place the rover 200 manually.

Figure 12:
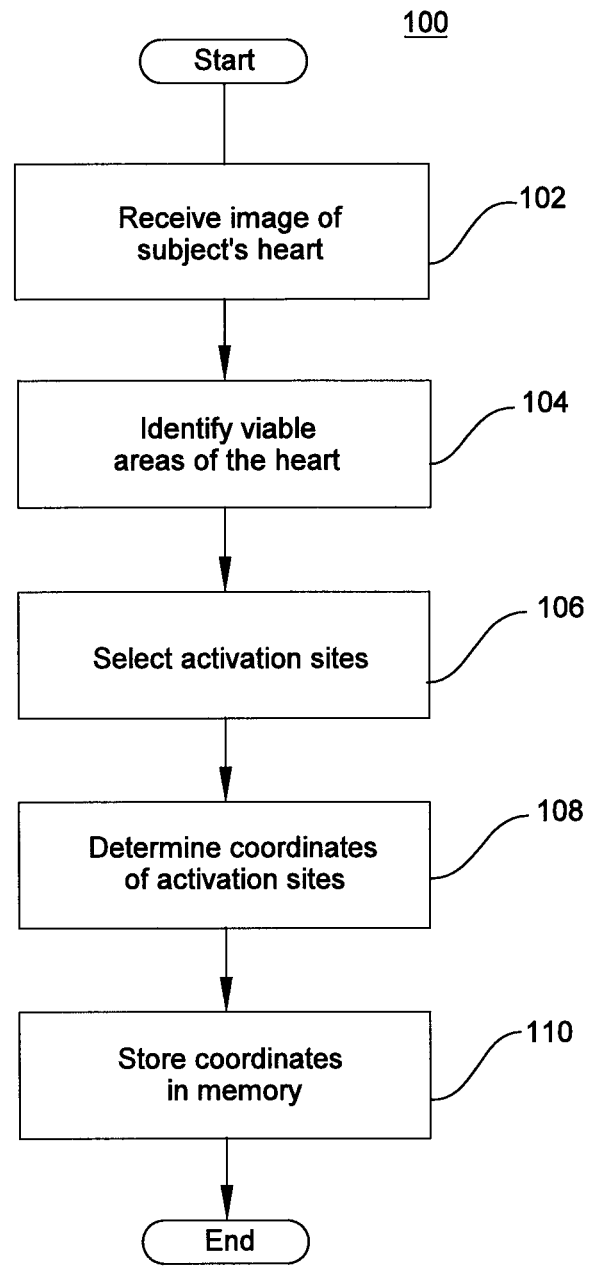
FIG. 12 is a flowchart of a process for determining activation sites of a subject's heart.

Referring to FIG. 12, a process 100 running on the control computer 84 determines the activation sites on or within a patient's heart. It is at these sites that one connects the four leads 14 of the pacemaker 12. Images of a subject's heart obtained by the imaging system 82 are received (block 102) at the control computer 84. From an analysis of the images, the most viable areas of the heart for lead placement can be determined. The most viable areas are generally the most electrically contractile and may also include other physical characteristics, such as muscle density, that makes them particularly suitable as activation sites Mapping for LV lead placement to optimal pacing sites may be chosen by performing preoperative and intraoperative hemodynamical and electrophysiological measurement. Echocardiography with tissue Doppler imaging may be performed in combination with electrophysiological measurements to determine the most delayed site of the left ventricular wall. Anatomically, the leads are placed in posterior to the obtuse marginal branch of the circumflex artery.

In one variation, the process 100 identifies (block 104) the most viable areas of the heart for lead placement. From the images, the process 100 selects (block 106) activation sites within the most viable areas and determines (block 108) the precise coordinates of the activation sites, for example by identifying which portion of each images depicts an area of the myocardium having a contractile activity greater than a predetermined threshold amount, or within a certain percentage of the maximum contractile activity for the entire heart. The control computer stores (block 110) the coordinates in memory. Alternatively, the identification and selection steps 104 and 106 may performed by a skilled practitioner (e.g. a surgeon or other medical professional) by examination of the images.

An iterative measurement process could also be used to identify the most viable areas of the heart for lead placement, as follows: (1) placing one or more electrodes against a selected location of the heart (e.g. by using the robotic arm 88 and/or the rover 200); (2) taking an impedance measurement at the selected location; (3) recording the impedance measurement; (4) repeating steps (1)-(3) at multiple spaced-apart locations, and (5) selecting the locations having the most desirable (e.g. lowest) impedance measurements as viable locations for lead placement.

Figure 13:
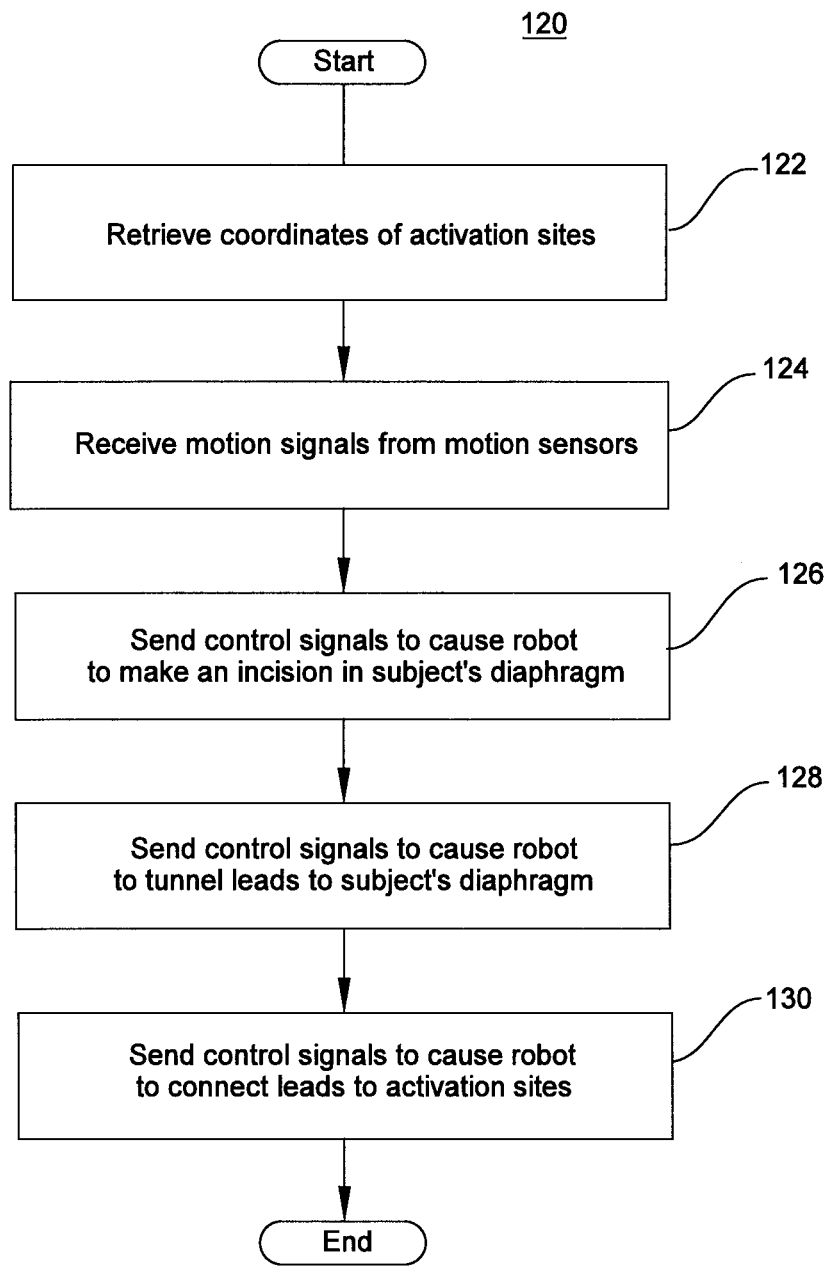
FIG. 13 is a flowchart of a process for robotic implantation of a pacemaker into a subject.

Referring to FIG. 13, a process 120 for directing the robotic mechanism 86 and/or the rover 200 to implant the pacemaker 12 into a subject is performed by the control computer 84. The process 120 retrieves (block 122) the coordinates that were previously determined using process 100 (FIG. 12) from memory. The control computer 84 receives (block 124) motion signals encoding the movement of a surgeon's hand. The control computer 84 controls the movement of the robotic arm 88 based on the motion signals such that it replicates the movement of the surgeon's hand. The control computer 84 sends (block 126) control signals that cause the robotic mechanism 86 to make a small incision in the patient's diaphragm. The control computer 84 sends (block 128) control signals that cause the robotic mechanism 86 and/or the rover 200 to implant the pulse generator 16 underneath the skin of the patient's torso (e.g., skin covering the abdomen) and to tunnel the leads 14 to the epicardial surface of the heart. The control computer 84 sends (block 130) control signals that cause the robotic mechanism 86 to connect the distal ends of the four leads 14 to the coordinates retrieved in step 122.

Figure 14:
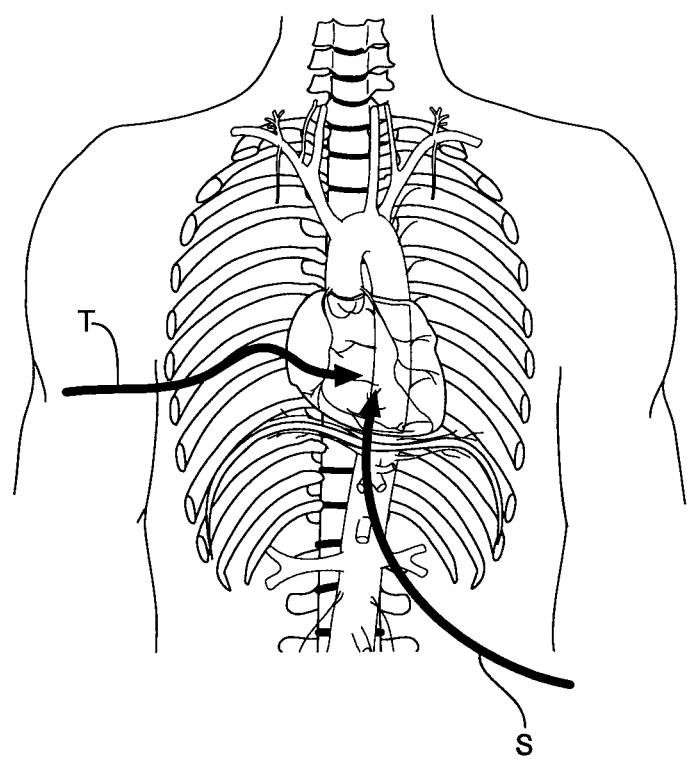
FIG. 14 is a schematic, partially-cut away view of a human subject, depicting paths for implantation of a pulse generator.

Regardless of whether the robotic arm 88 or the rover 200 is used, A path to the epicardium must be determined. FIG. 14 illustrates two possible pathways. The first path, shown by the arrow "T" is called a "mini-thoracotomy" where the operative channel passes, for example between the sixth and seventh ribs. Alternatively, in a subxiphoid approach, an incision will be made directly below the sternum. The surgeon then inserts the robotic arm 88 or rover 200 under the xypoid process and upward under the heart. This path is shown generally by the arrow "S".

A number of embodiments of the invention have been described. Nevertheless, it will be understood that various modifications may be made without departing from the spirit and scope of the invention. The foregoing are examples for illustration only and are not to limit the alternatives in any way. The processes described herein, including pacemaker process 60, activation site determination process 100, and robotic implantation process 120, can be implemented in digital electronic circuitry, or in computer software, firmware, or hardware, including the structural means disclosed in this specification and structural equivalents thereof, or in combinations of them. The processes can be implemented as one or more computer program products. More specifically, the processes can be implemented as one or more computer programs tangibly embodied in an information carrier (e.g., in a machine readable storage device or in a propagated signal) for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, subprograms, or portions of code). A computer program can be deployed to be executed on one computer or on multiple computers at one site or distributed across multiple sites and interconnected by a communication network. The processes described herein, including method steps, can be performed by one or more programmable processors executing one or more computer programs to perform functions of the processes by operating on input data and generating output. The processes can also be performed by, and apparatus of the processes can be implemented as, special purpose logic circuitry (e.g., an FPGA (field programmable gate array) or an ASIC (application specific integrated circuit)). In some embodiments, the pulse generator 16 may include multiple components selected from the components shown in FIG. 2, including multiple processors and memory blocks. Processors suitable for the execution of a computer program include, by way of example, both general and special purpose microprocessors, and anyone or more processors of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data (e.g., magnetic, magneto optical disks, or optical disks). Computer-readable media suitable for embodying computer program instructions and data include all forms of non volatile memory, including by way of example semiconductor memory devices (e.g., EPROM, EEPROM, and flash memory devices; magnetic disks (e.g., internal hard disks or removable disks; magneto optical disks; and CD ROM and DVD-ROM disks). The processor and the memory can be supplemented by, or incorporated in, special purpose logic circuitry. The processes can be implemented in a computing system that includes a back end component (e.g., a data server), a middleware component (e.g., an application server), or a front end component (e.g., a client computer having a graphical user interface or a Web browser through which a user can interact with an implementation of the processes), or any combination of such back end, middleware, and front end components. The components of the system can be interconnected by any form or medium of digital data communication (e.g., a communication network). Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other. Method steps associated with pacemaker process 60, activation site determination process 100, and robotic implantation process 120 can be rearranged and/or one or more of such steps can be omitted to achieve the same results described herein. Elements of different embodiments described herein may be combined to form other embodiments not specifically set forth above. Accordingly, other embodiments are within the scope of the following claims.

What is claimed is:

1. A system for pacing a heart, the system comprising:
an implantable pulse generator configured to generate electrical pacing impulses for stimulating contraction of cardiac tissue;
first, second, third, and fourth pacing leads in electrical communication with the pulse generator, each of the first, second, third, and fourth pacing leads configured to deliver the pacing impulses to activation sites within the cardiac tissue and to detect electrical cardiac activity at the activation sites; and a controller configured to control the delivery of the pacing impulses from each of the first, second, third, and fourth pacing leads, wherein the first pacing lead is configured to attach to an activation site located on the right atrium, the second pacing lead is configured to attach to an activation site located on the right ventricle, the third pacing lead is configured to attach to a posterior activation site on the left ventricle, and the fourth pacing lead is configured to attach to an anteriolateral activation site on the left ventricle.

2. The system of claim 1, further comprising a monitoring system in communication with the implantable pulse generator, the monitoring system configured to:

receive diagnostic data associated with the heart from the implantable pulse generator; and modify a pacing parameter of the implantable pulse generator based on the diagnostic data.

3. The system of claim 2, further comprising a communication relay device wirelessly coupled to the implantable pulse generator, the communication relay device configured to: relay the diagnostic data from the implantable pulse generator to the monitoring system; and relay commands for modifying the pacing parameter from the monitoring system to the implantable pulse generator.

4. The system of claim 2, wherein the monitoring system is further configured to: determine a medical condition of the heart from the diagnostic data, wherein the medical condition comprises heart failure, and wherein the diagnostic data includes volumetric measurements of the heart determined from impedance measurements acquired by at least two of the pacing leads across different vectors of the heart.

5. The system of claim 4, wherein the at least two of the pacing leads are configured to acquire the impedance measurements from epicardial sites of the heart.

6. The system of claim 2, wherein the pacing parameter comprises one or more of: pacing mode; amplitude, polarity, timing, and/or pulse width of the pacing impulses; ventricular sensitivity; atrial sensitivity; and rate of pacing the heart.

7. The system of claim 2, wherein the diagnostic data comprises one or more of: impedance measurements, telemetry and holter measurements, and heart failure analysis measurements.

8. The system of claim 1, wherein the first, second, third, and fourth pacing leads are configured to deliver the pacing impulses to activation sites that are electrically active sites determined to improve or optimize resynchronization of ventricular contraction.

9. The system of claim 1, wherein the first, second, third, and fourth pacing leads deliver pacing impulses to activation sites located in the myocardium of the right atrium, right ventricle, and left ventricle wherein the controller is further configured to direct the first, second, third, and fourth pacing leads to deliver the pacing impulses according to a pacing mode selected from the group consisting of: DOD, DO1, DVI, DOO, VDD, VVI, VOO, AAI, and AOO pacing modes.

10. The system of claim 1, wherein the controller is configured to direct the first, second, third, and fourth pacing leads to continuously deliver the pacing impulses to the activation sites, regardless of the speed of a beating rhythm of the heart.

11. The system of claim 1, wherein the controller is configured to direct at least two of the first, second, third, and fourth pacing leads to stimulate left and right ventricles of the heart at the same time.

12. The system of claim 1, wherein the controller is configured to direct at least two of the first, second, third, and fourth pacing leads to stimulate left and right ventricles of the heart at varied times.

13. The system of claim 1, wherein the controller is configured to receive atrial arrhythmia data from the implantable pulse generator and to modify a pacing parameter of the implantable pulse generator based on the atrial arrhythmia data.

14. The system of claim 1, wherein the controller is configured to receive diagnostic data associated with the heart from the implantable pulse generator and to generate data indicative of heart failure based on the diagnostic data.

15. The system of claim 1, wherein each of the pacing leads comprises a pacing electrode for attaching the lead to the respective activation sites, each of the pacing electrodes having at least one of a unipolar and bipolar configuration.

16. The system of claim 1, wherein each of the first, second, third, and fourth leads is configured to attach to its respective activation site without passing through the coronary sinus.

17. A method for pacing a heart with an implantable pulse generator comprising first, second, third, and fourth pacing leads, the implantable pulse generator configured to generate electrical pacing impulses for stimulating contraction of cardiac tissue, the method comprising:

placing the first pacing lead on the right atrium, placing the second pacing lead on the right ventricle, placing the third pacing lead at a posterior site on the left ventricle, and placing the fourth pacing lead at an anteriolateral site on the left ventricle;

delivering the pacing impulses through the first, second, third, and fourth pacing leads to activation sites within the cardiac tissue; and sensing electrical activity in the heart using each of the first, second, third, and fourth pacing leads.

18. The method of claim 17, further comprising: at a monitoring system, receiving diagnostic data associated with the heart from the implantable pulse generator; and modifying a pacing parameter of the implantable pulse generator based on the diagnostic data.

19. The method of claim 18, further comprising: relaying the diagnostic data from the implantable pulse generator to the monitoring system over a wireless communication channel; and relaying commands for modifying the pacing parameter from the monitoring system to the implantable pulse generator.

20. The method of claim 18, further comprising determining, using the monitoring system, a medical condition of the heart from the diagnostic data, wherein the medical condition comprises heart failure, and wherein the diagnostic data includes volumetric data related to the heart or a chamber therein and determined from impedance measurements acquired by at least two of the pacing leads across different vectors of the heart.

21. The method of claim 17, wherein modifying the pacing parameter of the implantable pulse generator comprises modifying one or more of: a pacing mode; an amplitude, a polarity, a timing, a pulse width of one or more of the pacing impulses, a ventricular sensitivity, an atrial sensitivity, and a rate of pacing the heart.

22. The method of claim 17, wherein the activation sites are electrically active sites determined to improve or optimize resynchronization of ventricular contraction.

23. The method of claim 17, wherein delivering the pacing impulses comprises delivering the pacing impulses according to a pacing mode selected from the group consisting of: DOD, 001, DYI, 000, YDD, WI, YOO, AAI, and AOO pacing modes.

24. The method of claim 23, wherein all of the pacing leads deliver pacing impulses to activation sites located in the heart, each pacing lead operably delivering a pacing impulse at timed intervals relative to other pacing leads.

25. The method of claim 17, wherein delivering the pacing impulses comprises delivering pacing impulses to activation sites located within the same ventricle of the heart using two of the first, second, third, and fourth pacing leads.

26. The method of claim 17, wherein delivering the pacing impulses comprises continuously delivering the pacing impulses to the activation sites, regardless of the speed of a beating rhythm of the heart.

27. The method of claim 17, wherein delivering the pacing impulses comprises stimulating left and right ventricles of the heart at the same time.

28. The method of claim 17, wherein delivering the pacing impulses comprises stimulating left and right ventricles of the heart at varied times.

29. The method of claim 17, further comprising receiving atrial arrhythmia data from the implantable pulse generator and modifying a pacing parameter based on the atrial arrhythmia data.

30. The method of claim 17, further comprising receiving diagnostic data associated with the heart from the implantable pulse generator and generating data indicative of heart failure based on the diagnostic data.

31. The method of claim 17, wherein placing comprises placing each of first, second, third, and fourth pacing leads without passing through the coronary sinus.

32. A system for pacing a heart, the system comprising:
an implantable pulse generator configured to generate electrical pacing impulses for stimulating contraction of cardiac tissue;
first, second, third, and fourth pacing leads in electrical communication with the pulse generator, each of the first, second, third, and fourth pacing leads configured to attach on an epicardial surface of the heart and deliver the pacing impulses to activation sites within the cardiac tissue and to detect electrical activity of the activation sites; and
a controller configured to control the delivery of the pacing impulses from each of the first, second, third, and fourth pacing leads,
wherein the first pacing lead is configured to attach to an activation site located on the right atrium, the second pacing lead is configured to attach to an activation site located on the right ventricle, the third pacing lead is configured to attach to a posterior activation site on the left ventricle, and the fourth pacing lead is configured to attach to an anterolateral activation site on the left ventricle.

33. A method for pacing a heart with an implantable pulse generator comprising first, second, third, and fourth pacing leads, the implantable pulse generator configured to generate electrical pacing impulses for stimulating contraction of cardiac tissue, the method comprising:
placing the first pacing lead on an epicardial surface of the right atrium, placing the second pacing lead on an epicardial surface of the right ventricle, placing the third pacing lead at a posterior site on an epicardial surface of the left ventricle, and placing the fourth pacing lead at an anterolateral site on an epicardial surface of the left ventricle;
delivering the pacing impulses through the first, second, third, and fourth pacing leads to activation sites within the cardiac tissue; and
sensing electrical activity in the heart using each of the first, second, third, and fourth pacing leads.

* * * * *